United States Patent
Kuebelbeck et al.

(10) Patent No.: US 10,065,993 B2
(45) Date of Patent: *Sep. 4, 2018

(54) PEPTIDES AND PEPTIDE/ACTIVE COMPOUND CONJUGATES FOR RENAL TARGETING

(71) Applicant: MERCK PATENT GMBH, Darmstadt (DE)

(72) Inventors: Armin Kuebelbeck, Bensheim (DE); Gregor Larbig, Gelnhausen (DE); Stefan Arnold, Muenster (DE); Walter Mier, Bensheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/890,059

(22) PCT Filed: Apr. 16, 2014

(86) PCT No.: PCT/EP2014/001026
§ 371 (c)(1),
(2) Date: Nov. 9, 2015

(87) PCT Pub. No.: WO2014/180534
PCT Pub. Date: Nov. 13, 2014

(65) Prior Publication Data
US 2016/0199505 A1    Jul. 14, 2016

(30) Foreign Application Priority Data
May 7, 2013  (EP) .................................... 13002432

(51) Int. Cl.
| A61K 38/00 | (2006.01) |
| C07K 14/00 | (2006.01) |
| A61K 31/192 | (2006.01) |
| A61K 31/381 | (2006.01) |
| C07K 7/06 | (2006.01) |
| A61K 51/08 | (2006.01) |
| C07K 7/08 | (2006.01) |
| A61K 47/64 | (2017.01) |

(52) U.S. Cl.
CPC .......... *C07K 14/001* (2013.01); *A61K 31/192* (2013.01); *A61K 31/381* (2013.01); *A61K 47/645* (2017.08); *A61K 51/08* (2013.01); *C07K 7/06* (2013.01); *C07K 7/08* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 4,645,661 A | 2/1987 | Schonbaum |
| 7,414,107 B2 | 8/2008 | Larsent et al. |
| 7,935,786 B2 | 5/2011 | Larsen et al. |
| 8,466,104 B2 | 6/2013 | Jonassen et al. |
| 8,563,508 B2 | 10/2013 | Jonassen et al. |
| 8,703,702 B2 | 4/2014 | Jonassen et al. |
| 9,078,929 B2 | 7/2015 | Kuebelbeck et al. |
| 2003/0135888 A1* | 7/2003 | Zhu ...................... C07K 14/415 800/288 |
| 2006/0063699 A1 | 3/2006 | Larsen et al. |
| 2007/0293418 A1 | 12/2007 | Larsen et al. |
| 2008/0015152 A1 | 1/2008 | Larsen et al. |
| 2008/0139785 A1 | 6/2008 | Larsen et al. |
| 2008/0227954 A1 | 9/2008 | Larsen et al. |
| 2008/0234467 A1 | 9/2008 | Larsen et al. |
| 2009/0069242 A1 | 3/2009 | Jonassen et al. |
| 2009/0208420 A1 | 8/2009 | Briel et al. |
| 2011/0312878 A1 | 12/2011 | Larsen et al. |
| 2012/0122788 A1 | 5/2012 | Kuebelbeck et al. |
| 2013/0217628 A1 | 8/2013 | Jonassen et al. |
| 2013/0252891 A1 | 9/2013 | Jonassen et al. |

FOREIGN PATENT DOCUMENTS

| WO | 9811126 A1 | 3/1998 |
| WO | 9946283 A1 | 9/1999 |
| WO | 0192469 A2 | 12/2001 |
| WO | 2007022774 A1 | 3/2007 |
| WO | 2008089738 A2 | 7/2008 |
| WO | 2011009539 A1 | 1/2011 |

OTHER PUBLICATIONS

Energetic contribution of solvent-exposed ion pairs to alpha-helix structure 1992 two pages.*
Pingchiang C. Lyu, Paul J. Gans, Neville R. Kallenbach, Energetic contribution of solvent exposed ion pairs to alpha-helix structure, Journal of Molecular Biology, vol. 223, Issue 1, Jan. 5, 1992, pp. 343-350. The reference is provided as a three page abstract from Science Direct Aug. 29, 2017.*
International Search Report for PCT/EP2014/001026 dated Aug. 6, 2014.
C. W. Cairo, et al., "Affinity-Based Inhibition of Beta-Amyloid Toxicity", Biochemistry, American Chemical Society, vol. 41, No. 27 (Sep. 2002) pp. 8620-8629.
P. C. Lyu, et al., "Energetic contribution of solvent-exposed ion pairs to alpha-helix structure", Journal of Molecular Biology, vol. 223, No. 1 (Jan. 1992) pp. 343-350.

(Continued)

*Primary Examiner* — Thomas S Heard
(74) *Attorney, Agent, or Firm* — Millen White Zelano and Branigan, PC; Csaba Henter

(57) ABSTRACT

The present invention relates to a peptide which consists of more than 50% of sequence sections of the formula -($A_n$-$B_m$-$C_o$)-, and to a conjugate containing the peptide and at least one covalently bonded active compound, and to a process for the preparation of the conjugate. The present invention furthermore relates to the use of the peptide and the conjugate for targeting of the kidney, and to a medicament comprising the peptide or conjugate.

20 Claims, 13 Drawing Sheets

Specification includes a Sequence Listing.

(56) References Cited

OTHER PUBLICATIONS

M. E. M. Dolman, et al., "Drug targeting to the kidney: Advances in the active targeting of therapeutics to proximal tubular cells", Advanced Drug Delivery Reviews, vol. 62, No. 14 (Nov. 2010) pp. 1344-1357.
E. J. F. Franssen, et al., "Low Molecular Weight Proteins as Carriers for Renal Drug Targeting. Preparation of Drug-Protein Conjugates and Drug-Spacer Derivatives and Their Catabolism in Renal Homogenates and Lysosmal Lysates", J. Med. Chem., vol. 35 (1992) pp. 1246-1259.
Z. Zhang, et al., "The targeting of 14-succiinate triptolide-lysozyme conjugate to proximal renal tubular epithelial cells", Biomaterials, vol. 30 (2009) pp. 1372-1381.
L. Denby, et al., Development of Renal-targeted Vectors Through Combined In Vivo Phage Display and Capsid Engineering of Adenoviral Fibers From Serotype 19p, Molecular Therapy, vol. 15, No. 9 (2007) pp. 1647-1654.
S. R. Kumar, et al., In-Labeled Galectin-3-Targeting Peptide as a SPECT Agent for Imaging Breast Tumors, The Journal of Nuclear Medicine, vol. 49, No. 5 (2008) pp. 796-803.
Q. Geng, et al., "Peptide-Drug Conjugate Linked via a Disulfide Bond for Kidney Targeted Drug Delivery", Bioconjugate, (2012) pp. 1200-1210.
G. T. Hermanson, "The Chemistry of Reactive Groups", Academic Press, (1996) pp. 137-165.
C.N. Salinas, et al., "The enhancement of chondrogenic differentiation of human mesenchymal stem cells by enzmatically regulated RGD functionalities", Biomaterials, No. 29 (2008) pp. 2370-2377.
R. Haag, et al., "Polymer Therapeutics: Concepts and Applications," Angew. Chem. Int. Ed., 2006, vol. 45, pp. 1198-1215.
G. B. Fields, et al. "Volume 289. Solid-Phase Peptide Synthesis", Print ISBN 978-0-12-182190-6, 1997.
P. Tyle, "Iontophoretic Devices for Drug Delivery", Pharmaceutical Research, vol. 3, No. 6 (1986) pp. 318-326.
W. C. Chan et al., "Fmoc Solid Phase Peptide Synthesis: A Practical Approach," Print ISBN 9780199637249, 2000.
M. I. Simon et al., "Volume 348. Protein Sensors and Reactive Oxygen Species, Part B: Thiol Enzymes and Proteins," Methods in enzymology, Print ISBN 978-0-12-182251-4, 2002.
Office Action—Notification of Reasons for Refusal Corresponding to JP 2016-512240—Date of Drafting: Apr. 18, 2018—dated May 15, 2018.

* cited by examiner

SEQUENCE LISTING

```
<160> NUMBER OF SEQ ID NOS: 91

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Pro Ala Ser Leu Tyr Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ile Thr Ser Leu Leu Ser
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Asn Thr Pro Cys Gly Pro Tyr Thr His Asp Cys Pro Val Lys Arg
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Lys Lys Lys
1

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Glu Glu Lys Lys Lys Lys Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Glu Lys Lys Lys Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Glu Lys Lys Lys
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Glu Lys Lys
1

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Glu Glu Lys Lys Lys Lys Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Glu Glu Lys Lys Lys Lys
1               5

<210> SEQ ID NO 11
<211> LENGTH: 6
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 11

Glu Glu Glu Lys Lys Lys
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Glu Glu Lys Lys
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Glu Glu Lys
1

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Glu Glu Glu Lys Lys Lys Lys Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Glu Glu Glu Lys Lys Lys Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Glu Glu Glu Lys Lys Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Glu Glu Glu Lys Lys
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Glu Glu Glu Glu Lys Lys Lys Lys Lys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Glu Glu Glu Glu Lys Lys Lys Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Glu Glu Glu Glu Lys Lys Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Glu Glu Glu Glu Glu Lys Lys
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Lys Lys Lys
1

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Asp Lys Lys Lys Lys Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asp Lys Lys Lys Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Lys Lys Lys
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asp Lys Lys
1

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Asp Asp Lys Lys Lys Lys Lys
1               5

<210> SEQ ID NO 28
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Asp Asp Lys Lys Lys Lys
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Asp Asp Lys Lys Lys
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Asp Asp Lys Lys
1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Asp Lys
1

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Asp Asp Asp Lys Lys Lys Lys Lys
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Asp Asp Asp Lys Lys Lys Lys
```

```
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Asp Lys Lys Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asp Asp Asp Lys Lys
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asp Asp Asp Asp Lys Lys Lys Lys Lys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Asp Asp Asp Asp Lys Lys Lys Lys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Asp Asp Asp Asp Lys Lys Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 39

Asp Asp Asp Asp Asp Asp Lys Lys
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Arg Arg Arg
1

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Glu Arg Arg Arg Arg Arg
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Glu Arg Arg Arg Arg
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Glu Arg Arg Arg
1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Glu Arg Arg
1

<210> SEQ ID NO 45

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Glu Glu Arg Arg Arg Arg Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Glu Glu Arg Arg Arg Arg
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Glu Glu Arg Arg Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Glu Glu Arg Arg
1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Glu Glu Arg
1

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Glu Glu Glu Glu Arg Arg Arg Arg Arg
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Glu Glu Glu Arg Arg Arg Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Glu Glu Glu Arg Arg Arg
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Glu Glu Glu Arg Arg
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Glu Glu Glu Glu Arg Arg Arg Arg Arg
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Glu Glu Glu Glu Arg Arg Arg Arg
1               5

<210> SEQ ID NO 56
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 56

Glu Glu Glu Glu Glu Arg Arg Arg
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Glu Glu Glu Glu Glu Arg Arg
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Lys Arg Lys
1

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Asp Lys Lys Arg Arg Lys
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Asp Lys Lys Lys Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Cys Lys Lys His
1               5
```

```
<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Asp Lys Lys
1

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Glu Glu Lys Lys Lys His Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Asp Asp Lys Lys Lys Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Asp Glu Arg Arg Arg
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Cys Glu Lys His
1               5

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67
```

Asp Glu Glu Lys
1

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Glu Asp Glu Arg Lys Arg Lys Arg
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Glu Glu Asp Lys Lys Lys His
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Asp Cys Glu Lys Arg His
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Asp Asp Glu Lys Lys
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Glu Glu Glu Glu Lys Lys Arg Arg Lys
1               5                   10

<210> SEQ ID NO 73
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 73

Glu Glu Glu Glu Asp Lys Lys Arg Lys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Asp Asp Glu Glu Lys Lys Arg
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asp Glu Glu Glu Glu Lys Lys
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Lys Glu Glu Glu
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Arg Glu Glu Glu
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Lys Glu Glu
1
```

```
<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Lys Lys Glu Glu Glu
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Lys Lys Glu Glu
1               5

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Arg Glu Glu Glu Arg Arg Glu Glu Glu Arg Arg Glu Glu Glu Arg
1               5                   10                  15

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Lys Glu Glu Lys Lys Glu Glu Lys Lys Glu Glu Lys Lys Glu Glu
1               5                   10                  15

Lys Lys Glu Glu Lys
            20

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Lys Lys Glu Glu Lys Lys Lys Glu Glu Lys Lys Lys Glu Glu Lys
1               5                   10                  15

<210> SEQ ID NO 84
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 84

Lys Lys Lys Glu Glu Glu Lys Lys Lys Glu Glu Glu Lys Lys Lys Glu
1               5                   10                  15

Glu Glu Lys

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Lys Glu Glu Glu Lys Lys Glu Glu Glu Lys Lys Glu Glu Glu Lys
1               5                   10                  15

<210> SEQ ID NO 86
<211> LENGTH: 4
<212> TYPE: PRT
<213> ORGANISM: Unknown
<220> FEATURE:
<223> OTHER INFORMATION: Description of Unknown:
      'DEVD' family peptide motif sequence

<400> SEQUENCE: 86

Asp Glu Val Asp
1

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Pro Glu Asn Phe Phe Trp Gly Gly Gly Gly
1               5                   10

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Pro Glu Asn Phe Phe
1               5

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Lys Lys Glu Glu Glu Lys Lys Glu Glu Glu Lys Lys Glu Glu Glu Lys
1               5                   10                  15
```

```
Lys Glu Glu Glu Lys Lys Glu Glu Glu Lys Lys Glu Glu Glu
            20              25              30

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Pro Ala Ser Leu Tyr Asn Ala Pro Ala Ser Leu Tyr Asn
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Lys Glu Glu Glu Lys Lys Glu Glu Glu Lys Lys Glu Glu Glu
1               5                   10                  15
```

PEPTIDES AND PEPTIDE/ACTIVE COMPOUND CONJUGATES FOR RENAL TARGETING

SEQUENCE LISTING

The instant application contains a Sequence Listing which has been submitted electronically in ASCII format and is hereby incorporated by reference in its entirety. Said ASCII copy, created on Feb. 9, 2016, is named MERCK-4392_SL.txt and is 20,036 bytes in size.

The present invention relates to a peptide which consists of more than 50% of sequence sections of the formula -$(A_n$-$B_m$-$C_o)$-, and to a conjugate containing the peptide and at least one covalently bonded active compound, and to a process for the preparation of the conjugate. The present invention furthermore relates to the use of the peptide and the conjugate for targeting of the kidney, and to a medicament comprising the peptide or conjugate.

The kidney is of importance, in particular, for the transport and excretion of various substances and in the production of hormones. One function of the kidneys is the excretion of end products of metabolism, the so-called urophanic substances, and toxins from the body through the formation of urine, which is finally excreted from the body via the urinary tract. The kidney regulates the water balance and thus serves for long-term regulation of blood pressure. It regulates the electrolyte balance and the acid-base balance by control of the composition of urine. Furthermore, the kidney is an important organ for intermediary metabolism in the body (it effects gluconeogenesis). The kidney produces hormones, such as, for example, erythropoietin, for blood formation and is the site of degradation of peptide hormones. However, many functions of the kidney itself are also controlled by hormones.

Today, about 280 million people suffer from chronic kidney diseases. Many diagnostic and therapeutic methods have already been developed. For example, immunosuppressants, cytostatics, immunotherapeutic agents, antiphlogistics, antibiotics, virostatics, antihypertensives, uricosurics, or diuretics are employed for the treatment of the kidney or for influencing kidney function. However, the use or dosage of medicaments for the treatment of kidney diseases is frequently restricted by side effects of the medicaments. It is therefore particularly important that the medicaments reach the kidney in as targeted a manner as possible.

Equally, representation of the kidney in imaging methods is also of major importance.

Established nuclear-medical and radiological methods, such as computer tomography (CT), SPECT (single-photon emission computer tomography), PET (positron emission tomography), ultrasound and MRT (magnetic resonance tomography), enable enzymatic processes, metabolic processes, the expression of certain genes and molecular reactions, besides morphological structures, to be depicted by so-called molecular imaging. The imaging modalities mentioned above can, if necessary, be further supplemented by computer tomographic and optical imaging methods (near-infrared imaging, fluorescence tomography). The focus of "molecular imaging" is at present still on the diagnosis of cancer diseases, neurological questions and the monitoring of gene therapies, but in the future will be extended to all areas in which cellular changes have to be discovered as early as possible. As signal source for the imaging methods, a "signal molecule" is generally coupled to a "carrier molecule". The "carrier molecule" ensures highly specific targeting by, for example, binding specifically to the target cells or becoming trapped therein. For example, the carrier molecule can be the ligand of a receptor or the substrate of an enzyme. The "signal molecule" can be rendered visible by means of one or more imaging techniques. Examples of signal molecules are, for example, complexing agents or chelating agents whose metal ions can be detected via imaging techniques. The compound or conjugate comprising signal molecule and carrier molecule is called the "diagnostic agent".

Investigations of the kidney are carried out, in particular, using renal scintigraphy. This is a nuclear-medical investigation method which allows the assessment of renal function from static and dynamic points of view. The blood supply, function and excretion of each individual kidney are assessed here. It is an established method for the recognition of parenchymal scarring, in particular in children, and furthermore serves for the assessment of regional and side-separated renal function.

In static renal scintigraphy, the functional kidney tissue is represented using the radionuclide $^{99m}$Tc. The technetium here is bound in complex form to, for example, 2,3-dimercaptosuccinic acid (DMSA). Static renal scintigraphy is therefore principally suitable for the representation of kidneys having anomalies (dystrophy, horseshoe kidney, etc.) or state after inflammation. By contrast, dynamic renal scintigraphy investigates renal function. Thus, the glomerular filtration rate, renal blood flow (RBF) and tubular secretion can be investigated with the question of renal function and clearance thereof.

Radiopharmaceuticals which are currently used are the following substances:

$^{99m}$Tc-MAG3 mercaptoacetyltriglycine
$^{99m}$Tc-DMSA 2,3-dimercaptosuccinic acid
$^{99m}$Tc-DTPA diethylenetriaminepentaacetic acid
$^{123}$I-OIH hippuran (ortho-iodohippuric acid)

It would therefore be desirable, for example, both for the depiction of the kidney in imaging methods and also for therapeutic purposes, if targeting of the kidney could be improved.

The prior art has already disclosed substances which are suitable for targeting of the kidney, i.e. for targeted transport into the kidney.

For example, it is known that relatively small endogenous proteins, such as lysozyme (14.3 kDa), are able to pass through the glomerulus of the kidneys and are suitable as transporters for addressing the kidneys with active compounds (Franssen et al.: *J. Med. Chem.* 35, 7, 1992, 1246-1259; Zhang et al.: *Biomaterials* 30, 2009, pp. 1372-1381). However, it is disadvantageous that lysozyme is a comparatively large molecule, meaning that the transporter to active compound ratio is unfavourable. In addition, the bonding of an active compound takes place non-specifically to one of the many reactive side groups present. This results in chemically undefined active compound/transporter mixtures. In addition, proteins such as lysozyme may have an immunogenic potential. The disadvantages of high-molecular-weight proteins do not apply on use of low-molecular-weight peptides.

The current literature furthermore describes various peptides having about 5 to 20 amino acids which are taken up selectively by the kidneys. These are, for example, APASLYN SEQ ID NO: 1) and HITSLLS (SEQ ID NO: 2) (Denby et al.: *Molecular Therapy* 15, 9, 2007, 1647-1654) or ANTPCGPYTHDCPVKR (SEQ ID NO: 3) (Kumar and Deutscher: *The Journal of Nuclear Medicine* 49, 5, 2008, 796-803; Geng et al.: *Bioconjugate Chemistry* 23, 2012, 1200-1210).

WO 2011/009539 A1 discloses active compound/ε-polylysine conjugates and the highly selective enrichment thereof in the kidney. The linking of the lysine units in the polymer takes place via their ε-amino groups. These compounds have a very long residence time in the kidney and are accordingly broken down relatively slowly.

Thus, there continued to be a demand for novel substances or carrier molecules ("carriers") which have the highest possible affinity and selectivity for the kidney. It was desirable here to find substances which, themselves or also as carrier molecules with their conjugated active compounds, can be broken down biochemically in the target cells of the kidney within an acceptable period.

The object of the present invention was therefore the provision of substances which are suitable for targeting of the kidney, in particular also as carrier molecule for a therapeutic agent or a diagnostic agent.

Surprisingly, it has been found that peptides of specific amino acid sequences and active compound conjugates thereof have very high selectivity for the kidney and can also be broken down again rapidly. The peptides can be employed as conjugates with signal molecules, such as, for example, radioisotopes and/or active compounds, for the diagnostic and/or therapeutic treatment of the kidney.

The present invention therefore relates to a peptide which consists of more than 50% (based on the number of amino acid units) of sequence sections of the formula (1)

$$-(A_n\text{-}B_m\text{-}C_o)-\qquad(1),$$

where
A stands for an amino acid having an acidic side group,
B stands for an amino group having a basic side group,
C stands for any desired amino acid,
n, m, independently of one another, stand for an integer from 1 to 10, where n:m=1:3 to 3:1,
o stands for an integer between 0 and 10,
and where
the peptide overall has a chain length of 5 to 100 amino acid units and
the peptide consists of at least 50% (based on the number of amino acid units) of amino acids A and B.

In accordance with the invention, a peptide is taken to mean a compound which has formed from linking of two or more amino acids via amide bonds. The individual amino acids here are connected in a defined sequence to form a chain.

In accordance with the invention, amino acids are compounds which carry at least one amino group and at least one carboxyl group. Examples are natural, proteinogenic amino acids or non-proteinogenic amino acids which occur in organisms or are prepared synthetically.

The amino acid units can be present in the D or L form in the peptide according to the invention.

In accordance with the invention, the peptide comprises 5 to 100 amino acids. In a preferred embodiment, the peptide has a chain length of 5 to 40 amino acid units, particularly preferably a chain length of 10 to 30 amino acid units.

In accordance with the invention, the peptide consists of more than 50% (based on the number of amino acid units) of sequence sections of the formula (1)

$$-(A_n\text{-}B_m\text{-}C_o)-\qquad(1).$$

It preferably consists of more than 70% of sequence sections of the formula (1), particularly preferably more than 90%.

In formula (1), A stands for an amino acid having an acidic side group. This can be, for example, aspartic acid, glutamic acid, argininosuccinate and/or cysteic acid. Preference is given to amino acids having a carboxyl function, i.e. glutamic acid and/or aspartic acid, particularly preferably glutamic acid.

Within a peptide, A may stand for different amino acids having acidic side groups, i.e., for example, both glutamic acid and also aspartic acid, argininosuccinate and/or cysteic acid residues may be present simultaneously in the peptide.

In an alternative embodiment, the amino acids having acidic side groups A within a sequence section of the peptide are identical; in this case, for example, all amino acids A of the formula (1) in one sequence section of the peptide stand for aspartic acid, glutamic acid, argininosuccinate or cysteic acid, and those in a further sequence section of the peptide stand, independently of the above-mentioned sequence section, for aspartic acid, glutamic acid or cysteic acid.

In a further alternative embodiment, the amino acids having acidic side groups A within the peptide are identical; in this case, all amino acids A of the peptide stand, for example, for aspartic acid, glutamic acid, argininosuccinate or cysteic acid.

In a preferred embodiment, all amino acids A within the peptide stand for glutamic acid.

n in formula (1) defines the number of amino acid units A. n here stands for an integer from 1 to 10. n preferably stands for an integer from 1 to 5, particularly preferably for 2 or 3.

In formula (1), B stands for an amino acid having a basic side group. This can be, for example, lysine, arginine, histidine and/or ornithine. Preference is given to lysine.

Within a peptide, B may stand for different amino acids having basic side groups, i.e., for example, both lysine, arginine, histidine and/or ornithine residues may be present simultaneously in the peptide.

In an alternative embodiment, the amino acids having basic side groups B within a sequence section of the peptide are identical; in this case, for example, all amino acids B of the formula (1) in one sequence section of the peptide stand for lysine, arginine, histidine or ornithine, and those in a further sequence section of the peptide stand, independently of the above-mentioned sequence section, for lysine, arginine, histidine or ornithine. In a further alternative embodiment, the amino acids having basic side groups B within the peptide are identical; in this case, all amino acids B of the peptide stand, for example, for lysine, arginine, histidine or ornithine. In a preferred embodiment, all amino acids B within the peptide stand for lysine.

m in formula (1) defines the number of amino acid units B. m here stands for an integer from 1 to 10. m preferably stands for an integer from 1 to 5, particularly preferably for 2 or 3.

In formula (1), C stands for any desired amino acid. This can be, for example, alanine, arginine, asparagine, cysteine, glutamine, glycine, histidine, isoleucine, leucine, lysine, methionine, phenylalanine, proline, serine, threonine, tryptophan, tyrosine, valine and/or citrulline.

Preference is given to proteinogenic amino acids which are linked in a natural manner. This ensures degradation of the peptide in the proximal tubule cells of the kidneys to give toxicologically entirely benign metabolites. Within a peptide, C may stand for different amino acids.

o in formula (1) defines the number of amino acid units C. o here stands for an integer from 0 to 10. o preferably stands for 0, 1 or 2, particularly preferably for 0 or 1. In a very particularly preferred embodiment, o stands for 0, i.e. in this case no amino acid unit C is present in the peptide.

In a preferred embodiment, n and m stand, independently of one another, for 2 or 3.

In accordance with the invention, the ratio of n:m in formula (1) is 1:3 to 3:1. Illustrative embodiments of the sequence sections of the formula (1) are: -($A_1$-$B_3$-$C_o$)-, -($A_1$-$B_2$-$C_o$)-, -($A_1$-$B_1$-$C_o$)-, -($A_2$-$B_6$-$C_o$)-, -($A_2$-$B_5$-$C_o$)-, -($A_2$-$B_4$-$C_o$)-, -($A_2$-$B_3$-$C_o$)-, -($A_2$-$B_2$-$C_o$)-, -($A_2$-$B_1$-$C_o$)-, -($A_3$-$B_9$-$C_o$)-, -($A_3$-$B_8$-$C_o$)-, -($A_3$-$B_7$-$C_o$)-, -($A_3$-$B_6$-$C_o$)-, -($A_3$-$B_5$-$C_o$)-, -($A_3$-$B_4$-$C_o$)-, -($A_3$-$B_3$-$C_o$)-, -($A_3$-$B_2$-$C_o$)-, -($A_3$-$B_1$-$C_o$)-, -($A_4$-$B_{10}$-$C_o$)-, -($A_4$-$B_9$-$C_o$)-, -($A_4$-$B_8$-$C_o$)-, -($A_4$-$B_7$-$C_o$)-, -($A_4$-$B_6$-$C_o$)-, -($A_4$-$B_5$-$C_o$)-, -($A_4$-$B_4$-$C_o$)-, -($A_4$-$B_3$-$C_o$)-, -($A_4$-$B_2$-$C_o$)-, -($A_5$-$B_{10}$-$C_o$)-, -($A_5$-$B_9$-$C_o$)-, -($A_5$-$B_8$-$C_o$)-, -($A_5$-$B_7$-$C_o$)-, -($A_5$-$B_6$-$C_o$)-, -($A_5$-$B_5$-$C_o$)-, -($A_5$-$B_4$-$C_o$)-, -($A_5$-$B_3$-$C_o$)-, -($A_5$-$B_2$-$C_o$)-, -($A_6$-$B_{10}$-$C_o$)-, -($A_6$-$B_9$-$C_o$)-, -($A_6$-$B_8$-$C_o$)-, -($A_6$-$B_7$-$C_o$)-, -($A_6$-$B_6$-$C_o$)-, -($A_6$-$B_5$-$C_o$)-, -($A_6$-$B_5$-$C_o$)-, -($A_6$-$B_3$-$C_o$)-, -($A_6$-$B_2$-$C_o$)-, -($A_7$-$B_{10}$-$C_o$)-, -($A_7$-$B_9$-$C_o$)-, -($A_7$-$B_8$-$C_o$)-, -($A_7$-$B_7$-$C_o$)-, -($A_7$-$B_6$-$C_o$)-, -($A_7$-$B_5$-$C_o$)-, -($A_7$-$B_4$-$C_o$)-, -($A_7$-$B_3$-$C_o$)-, -($A_8$-$B_{10}$-$C_o$)-, -($A_8$-$B_9$-$C_o$)-, -($A_8$-$B_8$-$C_o$)-, -($A_8$-$B_7$-$C_o$)-, -($A_8$-$B_6$-$C_o$)-, -($A_8$-$B_5$-$C_o$)-, -($A_8$-$B_4$-$C_o$)-, -($A_8$-$B_3$-$C_o$)-, -($A_9$-$B_{10}$-$C_o$)-, -($A_9$-$B_9$-$C_o$)-, -($A_9$-$B_8$-$C_o$)-, -($A_9$-$B_7$-$C_o$)-, -($A_9$-$B_6$-$C_o$)-, -($A_9$-$B_5$-$C_o$)-, -($A_9$-$B_4$-$C_o$)-, -($A_9$-$B_3$-$C_o$)-, -($A_{10}$-$B_{10}$-$C_o$)-, -($A_{10}$-$B_9$-$C_o$)-, -($A_{10}$-$B_8$-$C_o$)-, -($A_{10}$-$B_7$-$C_o$)-, -($A_{10}$-$B_6$-$C_o$)-, -($A_{10}$-$B_5$-$C_o$)- or -($A_{10}$-$B_4$-$C_o$)-, where A, B, C and o are defined as described above.

In accordance with the invention, the sequence of the formula (1) can stand, for example, for a sequence selected from -(EKKK)- (SEQ ID NO: 4), -(EKK)-, -(EK)-, -(EEKKKKK)- SEQ ID NO: Q, -(EEKKKK)- (SEQ ID NO: 6), -(EEKKK)- (SEQ ID NO: 7), -(EEKK)- (SEQ ID NO: 8), -(EEK)-, -(EEEKKKKK)- (SEQ ID NO: 9), -(EEEKKKK)- (SEQ ID NO: 10), -(EEEKKK)- SEQ ID NO: 11), -(EEEKK)- (SEQ ID NO: 12), -(EEEK)- (SEQ ID NO: 13), -(EEEEKKKKK)- SEQ ID NO: 14), -(EEEEKKKK)- (SEQ ID NO: 15), -(EEEEKKK)- (SEQ ID NO: 16), -(EEEEKK)- SEQ ID NO: 17), -(EEEEEKKKKK)- (SEQ ID NO: 18), -(EEEEEKKKK)- (SEQ ID NO: 19), -(EEEEEKKK)-(SEQ ID NO: 20), -(EEEEEKK)- (SEQ ID NO: 21), -(DKKK)- (SEQ ID NO: 22), -(DKK)-, -(DK)-, -(DDKKKKK)- (SEQ ID NO: 23), -(DDKKKK)- (SEQ ID NO: 24), -(DDKKK)- (SEQ ID NO: 25), -(DDKK)- (SEQ ID NO: 26), -(DDK)-, -(DDDKKKKK)- (SEQ ID NO: 27), -(DDDKKKK)-(SEQ ID NO: 28), -(DDDKKK)- (SEQ ID NO: 29), -(DDDKK)- (SEQ ID NO: 30), -(DDDK)-(SEQ ID NO: 31), -(DDDDKKKKK)- (SEQ ID NO: 32), -(DDDDKKKK)- (SEQ ID NO: 33), -(DDDDKKK)- (SEQ ID NO: 34), -(DDDDKK)- (SEQ ID NO: 35), -(DDDDDKKKKK)- (SEQ ID NO: 36), -(DDDDDKKKK)- (SEQ ID NO: 37), -(DDDDDKKK)- (SEQ ID NO: 38), -(DDDDDDKK)-(SEQ ID NO: 39), -(ERRR)- (SEQ ID NO: 40), -(ERR)-, -(ER)-, -(EERRRRR)-(SEQ ID NO: 41), -(EERRRR)- (SEQ ID NO: 42), -(EERRR)- (SEQ ID NO: 43), -(EERR)- (SEQ ID NO: 44), -(EER)-, -(EEERRRRR)- (SEQ ID NO: 45), -(EEERRRR)- (SEQ ID NO: 46), -(EEERRR)-(SEQ ID NO: 47), -(EEERR)- (SEQ ID NO: 48), -(EEER)- (SEQ ID NO: 49), -(EEEERRRRR)-(SEQ ID NO: 50), -(EEEERRRR)- (SEQ ID NO: 51), -(EEEERRR)- SEQ ID NO: 52), -(EEEERR)- (SEQ ID NO: 53), -(EEEEERRRRR)- (SEQ ID NO: 54), -(EEEEERRRR)-(SEQ ID NO: 55), -(EEEEERRR)- (SEQ ID NO: 56), -(EEEEEERR)- (SEQ ID NO: 57), -(EKRK)- (SEQ ID NO: 58), -(ERK)-, -(EDKKRRK)- (SEQ ID NO: 59), -(EDKKKK)- SEQ ID NO: 60), -(ECKKH)- (SEQ ID NO: 61), -(EDKK)- (SEQ ID NO: 62), -(DEEKKKHK)- (SEQ ID NO: 63), -(EDDKKKK)- (SEQ ID NO: 64), -(EDERRR)- (SEQ ID NO: 65), -(DCEKH)- (SEQ ID NO: 66), -(DEEK)-(SEQ ID NO: 67), -(DEDERKRKR)- (SEQ ID NO: 68), -(DEEDKKKH)- (SEQ ID NO: 69), -(EDCEKRH)- (SEQ ID NO: 70), -(EDDEKK- (SEQ ID NO: 71), -(EEEEEKKRRK)- (SEQ ID NO: 72), -(EEEEDK-KRK)- (SEQ ID NO: 73), -(EDDEEEKKR)- (SEQ ID NO: 74), -(DDEEEEKK)-(SEQ ID NO: 75), in each of which the one-letter codes of the amino acids are used: E (glutamic acid), D (aspartic acid), C (cysteine), K (lysine), R (arginine), H (histidine). The sequence of the formula (1) preferably stands for a sequence selected from the group comprising -(KKEEE)- (SEQ ID NO: 76), -(RREEE)- (SEQ ID NO: 77), -(KKEE)- SEQ ID NO: 78), -(KKKEEE) (SEQ ID NO: 79) and -(KKKEE)- (SEQ ID NO: 80). The sequence of the formula (1) particularly preferably stands for the sequence -(KKEEE)- (SEQ ID NO: 76):

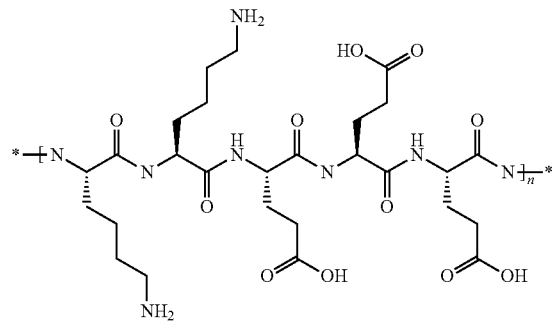 [SMILES: *NC(=O)[C@H](CCC(=O)O)NC(=O)[C@H](CCC(=O)O)NC(=O)[C@H](CCC(=O)O)NC(=O)[C@H](CCCCN)NC(=O)[C@H](CCCCN)N*]

In accordance with the invention, the peptide consists of at least 50% (based on the number of amino acid units) of amino acids A and B. The peptide preferably consists of at least 70% (based on the number of amino acid units) of amino acids A and B, particularly preferably at least 80%.

In accordance with the invention, the sequence section of the formula (1) may be present in the peptide in total 1 to 50 times, preferably 1 to 30 times, particularly preferably 1 to 10 times, especially preferably 2 to 5 times.

In a possible embodiment, the peptide contains a plurality of directly successive sequence sections of the formula (1). The peptide preferably contains 3 to 5 successive sequence sections of the formula (1).

For example, the peptide may consist of 3 to 5 successive sequence sections of the formula (1) and one or more further amino acids at the C and/or N terminal. This is illustrated in formula (2):

$$X_p(A_nB_mC_o)_xY_q \qquad (2)$$

in which A, B, C, n, m and o are as defined above,
x stands for 3, 4, or 5,
X and Y stand, independently of one another, for any desired amino acid, preferably for A, and
p and q stand, independently of one another, for an integer between 0 and 3, preferably for 0 or 1.

Examples of possible peptides are peptides selected from the group comprising (RREEE)$_3$R (SEQ ID NO: 81), (KKEE)$_5$K (SEQ ID NO: 82), (KKKEE)$_3$K (SEQ ID NO: 83), (KKKEEE)$_3$K (SEQ ID NO: 84) and (KKEEE)$_3$K (SEQ ID NO: 85).

The present invention furthermore also relates to a conjugate containing at least one peptide, as defined above, and at least one active compound bonded covalently, optionally via a spacer.

In accordance with the invention, one or more identical or different active compound molecules may be bonded per conjugate according to the invention.

Equally, the conjugate according to the invention, in particular in the case of macromolecules, such as relatively large active compound molecules, for example proteins, may also contain two or more peptides which are bonded to an active compound molecule in order to facilitate kidney-specific concentration of the active compound. The peptides are typically again covalently bonded to the macromolecule here. In accordance with the invention, macromolecules are taken to mean not only large molecules such as proteins, but instead also any form of particles (for example nanoparticles), liposomes or other systems by means of which active compounds can be transported or bonded to the active compounds.

In accordance with the invention, an active compound is taken to mean any substance which can be coupled to the oligomer in order to employ it for diagnostic and/or therapeutic treatment. In accordance with the invention, it can thus be either a signal molecule or a "classical" active compound.

In accordance with the invention, active compounds or active-compound molecules in accordance with the German Medicines Act are substances which are intended to be used as pharmaceutically active constituents in the preparation of medicaments or to become pharmaceutically active constituents on use in the preparation of medicaments (German Medicines Act § 4 (19)). Active compounds generally cause a specific effect in an organism. An active compound according to the invention is typically a pharmaceutically active molecule or medicament, such as, for example, immunosuppressants, for example azathioprine, mycophenolate-mofetil, ciclosporin, tacrolimus, sirolimus, fingolimod or triptolide, cytostatics, for example atrasentan, nintedanib, bleomycin, dactinomycin, mitomycin, daunorubicin, doxorubicin, epirubicin, idarubicin, mitoxantron, amsacrine, doxofluridine, cisplatin, carboplatin, oxaliplatin, satraplatin, camptothecin, toptecan, irinotecan, etoposide, teniposide, cyclophosphamide, trofosfamide, melphalan, chlorambucil, estramustine, busulfan, chlorambucil, chlormethine, treosulfan, carmustine, lomustine, nimustine, procarbazine, streptozocine, dacarbazine, ifosfamide, temozolomide, thiotepa, vinorelbine, vincristine, vinblastine, vindesine, paclitaxel, docetaxel, methotrexate, pemetrexed, raltitrexed, fluorouracil, capecitabine, cytosinarabinoside, gemcitabine, tioguanine, pentostatin, mercaptopurine, fludarabine, caldribine, hydroxycarbamide, mitotane, azacitidine, cytarabine, nelarabine, bortezomib, anagrelide, in particular the protein kinase inhibitors, such as, for example, imatinib, erlotinib, sunitinib, sorafenib, dasatinib, lapatinib or nilotinib, immunotherapeutic agents, for example cetuximab, alemtuzumab and bevacizumab, antiphlogistics, for example naproxen, ibuprofen, indometacin, prednisolone, prednisone, hydrocortisone or budesonide, antibiotics, in particular the penicillins, such as, for example, benzylpenicillin, methicillin or amoxicillin, the cephalosporins, such as, for example, cefuroxim, cefotaxim, cefadroxil or cefixim, the -lactamase inhibitors, such as, for example, clavulanic acid, sulbactam or tazobactam, the carbapenems, such as, for example, imipenem or meropenem, the monobactams, such as, for example, aztreonam, the tetracyclines, such as, for example, tetracycline, chlortetracycline, oxytetracycline, doxycycline, minocycline or tigecycline, the macrolide antibiotics, such as, for example, erythromycin A, the glycopeptide antibiotics, such as, for example, vancomycin, the enediynes, such as, for example, calicheamicin, virostatics, for example aciclovir, valaciclovir, ganciclovir, valganciclovir, penciclovir, famciclovir, brivudine, cidofovir, foscarnet, idoxuridine or tromantadine, antihypertensives, in particular the ACE inhibitors, such as, for example, benazepril, captopril, cilazapril, enalapril, fosinopril, lisinopril, perindopril, quinapril, ramipril, trandolapril or zofenopril, the sartans, such as, for example, losartan, balsartan, irbesartan, candesartan, eprosartan, olmesartan or telmisartan, the renin inhibitors, such as, for example, aliskiren, and the beta blockers, such as, for example, proproanolol, pindolol, sotalol, bopindolol, atenolol, bisorpolol, celiprolol, esmolol, metoprolol, nebivolol, oxprenolol, carvedilol or labetalol, uricosurics, for example probenecid or benzbromarone, or diuretics, for example acetazolamide, furosemide, torasemide, bumetanide, piretanide, azosemide, etacrynic acid, etozoline, hydrochlorothiazide, benzthiazide, chlorothiazide, chlorthalidone, indapamide, mefruside, metolazone, clopamide, xipamide, hydroflumethiazide, methyclothiazide, polythiazide, amiloride, triameterene, spironolactone, canrenone, eplerenone or spironolactone, antifibrotics, for example pirfenidone or seliciclib.

Further antitumour agents, for example agents which are effective against proliferating cells, are in accordance with the invention likewise active compounds. Illustrative antitumour agents include cytokines, such as, for example, interleukin-2 (IL-2), tumour necrosis factor or the like, lectin inflammation reaction promoters (selectins), such as, for example, L-selectin, E-selectin, P-selectin or the like, and similar molecules.

In addition to the active-compound molecules, or instead of the active-compound molecules, other functionalities, such as, for example, functionalities for diagnostic or imaging methods, may also be bonded to the conjugate according to the invention.

Equally, fluorine-containing side chains can be incorporated as functionality via optional spacers. The accumulation of the corresponding molecules in the kidneys can thus be represented with the aid of $^{19}F$ nuclear resonance tomography. Highly symmetrically arranged fluorine atoms, which have a uniform resonance frequency, are particularly advantageous here. In order to improve the $^{19}F$ signal, a contrast agent which is usual in nuclear spin tomography, such as, for example, gadobutrol (Magnevist®), can be used.

Complexing agents may likewise be present in the conjugate as "active compound". In accordance with the invention, a complexing agent is any molecular structure which is capable of complexing metal ions, i.e. of forming a metal-chelate complex with the metal ions. Complexing agents are frequently also known as chelating agents. Examples of complexing agents which are suitable in accordance with the invention are EDTA, NOTA, TETA, iminodiacetic acid, DOTA or DTPA. Particular preference is given in accordance with the invention to complexing agents which bind metal ions which can be detected in SPECT, PET, CT or MRT measurements. Preferred complexing agents are DOTA or DTPA or derivatives thereof. In accordance with the invention, complexing agents are both molecules to which the metal ions are already bonded and also molecules to which metal ions can be bonded, but are not bonded at the present stage.

Metal ions which are suitable in accordance with the invention for bonding to complexing agents are, for example, $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and/or $Mn^{2+}$ or also the ions of radionuclides, such as gamma emitters, positron emitters, Auger electron emitters, alpha emitters and fluorescence emitters, for example $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{88}Y$, $^{90}Y$, $^{149}Pm$, $^{177}Lu$, $^{47}Sc$, $^{142}Pr$, $^{159}Gd$, $^{212}Bi$, $^{72}As$, $^{72}Se$, $^{97}Ru$, $^{109}Pd$, $^{105}Rh$, $^{101m}Rh$, $^{119}Sb$, $^{128}Ba$, $^{197}Hg$, $^{211}At$, $^{169}Eu$, $^{203}Pb$, $^{212}Pb$, $^{64}Cu$, $^{67}Cu$, $^{188}Re$, $^{186}Re$, $^{198}Au$ and/or $^{199}Ag$.

Examples of suitable metal ions and their respective use are:
$^{111}$In for SPECT
$^{68}$Ga for PET
$^{90}$Y for therapy
Gd, Eu, Mn for MRT
tantalum, tungsten or other elements having a high atomic number for computer tomography If the conjugate according to the invention comprises complexing agents, it is particularly advantageous to integrate gadolinium or manganese or another strongly paramagnetic metal ion which is known to the person skilled in the art with the aid of a complexing agent located on the conjugate according to the invention. Suitable complexing agents here are, for example, DOTA and DTPA.

Furthermore, complexing agents, such as hydroxyquinoline, thiourea, guanidine, dithiocarbamate, hydroxamic acid, amidoxime, aminophosphoric acid, (cyclic) polyamino, mercapto, 1,3-dicarbonyl and crown ether radicals having in some cases very specific activities with respect to ions of different metals, can be conjugated—also optionally via spacers.

Functionalities for cell-specific targeting, such as, for example, antibodies, antibody fragments or aptamers, may also be bonded to the conjugate according to the invention. Fluorescent dyes or interleukins, such as IL-2, may also be bonded.

Active compounds, peptides, complexing agents or other functionalities can be covalently bonded to the peptide directly or by means of a spacer.

A spacer, often also called linker, effects a covalent bond between two parts of a molecule, in the present case, for example, between the peptide and an active compound. A spacer is introduced, for example, if the connection between two moieties is not to take place only via a direct chemical bond, but instead a certain separation is to be generated between two moieties. Equally, a spacer can provide the chemical functionalities which are necessary in order to connect two parts of a molecule which would otherwise not react with one another. The conjugation of a spacer onto the peptide or an active compound preferably takes place via an amide or ester bond. Spacers can be, for example, aliphatic hydrocarbons, polyethers (such as polyethylene glycols), peptides or similar elements having a chain structure. The spacer may be stable, i.e. it can only be cleaved to a slight extent or not at all under physiological conditions, or it may be unstable, i.e. it can be cleaved at least under certain physiological conditions.

Examples of functional groups via which direct bonding can take place are —NH$_2$, —SH, —OH, -Hal (e.g. —Cl, —Br, —I), -alkyne, —NCS, —NCO, SO$_2$Cl, -azide, -carbonate, -aldehyde, -epoxide, —COOH, —COOR, where R in this case is preferably a halogen or preferably an activator, i.e. a good leaving group, for example N-hydroxysuccinimide, pentafluorophenyl or para-nitrophenyl. An overview of possible covalent types of coupling can be found, for example, in "Bioconjugate Techniques", Greg T. Hermanson, Academic Press, 1996 on pages 137 to 165.

For example, active compounds may be bonded via a cleavable linker in the conjugate according to the invention. This linker is then cleaved in vivo under certain conditions, for example enzymatically or chemically, and releases the active compound. For this purpose, suitable linkers are those which contain carboxylate and disulfide bonds, in which the former groups are hydrolysed enzymatically or chemically and the latter are separated off by disulfide exchange, for example in the presence of glutathione.

An example of a cleavable spacer is also a peptide which can be cleaved specifically with the aid of specific, endogenous enzymes or alternatively those which are added to the body. Thus, for example, the peptide sequence DEVD (Asp-Glu-Val-Asp (SEQ ID NO: 86)) is cleaved after apoptosis induction by caspase-3. For example, an active compound which is bonded via a spacer of this type can thus be removed from the kidney after a certain residence time therein, or alternatively a corresponding functionality (presence or absence of a certain enzyme) of the kidney can be checked. Further examples are the peptide sequences CPEN1FFWGGGG (SEQ ID NO: 87) (Salinas et al. 2008, Biomaterials 29, 2370-2377) or PENFF (SEQ ID NO: 88), which can be cleaved by the matrix metalloprotease-13.

A simple embodiment of a cleavable spacer is the formation of a carboxylate, which can easily be cleaved by esterases.

In a preferred embodiment of the present invention, the active compound is therefore bonded via an ester link. This enables precise cleaving-off of the active compound molecule in the kidney. At the same time, however, the link is previously sufficiently stable for transport into the kidney in order to prevent premature cleaving-off.

Furthermore, a readily cleavable ester link of the active compound to the active compound transporter enables relatively fast release of the active compound at the target site. The cleavage of the ester link takes place more quickly in terms of time than the degradation of the active compound transporter by proteases.

Alternatively, the spacer may contain an acid-labile structure, for example a hydrazone, an imine, a carboxylhydrazone, an acetal or ketal (see, for example, Haag-R, Kratz-F, Angewandte Chemie page 1218 (2006)).

Carbonates are advantageous for conjugation of active compounds having aliphatic or aromatic hydroxyl groups. They can be synthesised simply and in high yield from the corresponding alcohols or phenols by reaction with chloroformates. The reaction with chloroformates which contain a triple bond, such as, for example, propargyl chloroformate (CAS Number 35718-08-2), is particularly advantageous here. The triple bond introduced in this way enables the carbonates, which can easily be cleaved enzymatically, to be linked to azides which have been incorporated into the peptide oligomer, by means of 1,3-dipolar cycloaddition, the so-called Huisgen reaction, simply and under very gentle conditions.

The same applies to the conjugation of aliphatic or aromatic amino groups with the aid of chloroformates. Instead of the carbonates, the corresponding carbamates, which can likewise be cleaved easily by esterases, form here. Here too, linking to chloroformates which contain a triple bond is particularly advantageous.

In accordance with the invention, the at least one active compound can be bonded to the N and/or C terminal of the peptide.

In an alternative embodiment, the active compound can be bonded to an amino acid in the chain.

In a further alternative embodiment, the active compound can be bonded in the chain between the amino acids.

The peptide according to the invention and its active compound conjugate are taken up highly selectively by the kidneys and broken down relatively rapidly.

A suitable choice of the chain length and molecular structure of the peptide, and the suitable choice of the linking site of the active compound on the peptide, enables the desired pharmacokinetics, i.e. the desired active compound release at the target site, i.e. in the kidney, to be established here.

Typically, longer peptides result in delayed release compared with shorter peptides. Longer peptides have, for example, chain lengths of 20 to 40 amino acids, preferably 30 amino acids, while shorter peptides are typically taken to mean chain lengths of 3 to 10 amino acid, preferably 5 amino acids.

The release of active compounds linked at the C terminal takes place significantly more quickly than that of active compounds linked at the N terminal. Without being tied to this theory, it is assumed that the rate-determining step in peptide degradation is influenced, in particular, by carboxypeptidases, which break down the peptide starting from the C terminal.

In accordance with the invention, active compounds incorporated into the chain in a branched manner are also released significantly more slowly than those linked in a linear manner. The enzymatic degradation of branched peptide structures is basically significantly more difficult than the degradation of linear peptides.

Furthermore, the release rate of the active compound can, in accordance with the invention, also be controlled by the type of linking thereof to the oligomer. A readily cleavable ester link enables relatively fast release of the active compound at the target site (see above).

The present invention also relates to a process for the preparation of a conjugate, as described above, characterised in that an optionally activated active compound is conjugated onto the peptide.

The preparation of the conjugates according to the invention typically has at least the following process steps:
a) provision of a peptide according to the invention which contains at least one reactive group,
b) conjugation of at least one optionally activated active compound onto the peptide from step a).

In an embodiment of the process according to the invention, if the conjugate contains a complexing agent as active compound, the compound obtained in step b) is brought into contact, in a further step c), with metal salts, so that metal ions are complexed by the complexing agents.

The peptides of the conjugates according to the invention can be prepared, in particular, by various processes known to the person skilled in the art in the area of peptide synthesis.

The preparation is typically carried out via a solid-phase synthesis.

In accordance with the invention, a solid phase is an organic, inorganic or organic/inorganic composite material which can be employed as resin or support in solid-phase synthesis. Furthermore, surfaces of mouldings, such as, for example, microtitre plates or particulate materials, such as, for example, organic or inorganic nanoparticles, metal particles or the like, are also regarded as solid phase in accordance with the invention.

The solid-phase synthesis is carried out in a corresponding manner to a conventional peptide synthesis (for example Fmoc/tBu peptide synthesis or Boc/benzyl peptide synthesis). Solid-phase syntheses of this type are known to the person skilled in the art. Suitable textbooks for peptide synthesis are "Solid-Phase Peptide Synthesis": 289 (Methods in Enzymology) by Sidney P. Colowick (author), Gregg B. Fields (publisher), Melvin I. Simon (publisher) Academic Press Inc (November 1997) or "Fmoc Solid Phase Peptide Synthesis: A Practical Approach" by W. Chan (author), W. C. Chan (publisher), Peter D. White (publisher) "Oxford Univ Pr (2 Mar. 2000). The monomers employed in each case are selected here in such a way that a peptide corresponding to the present invention is formed. Depending on the type of amino acid unit, the synthesis can be carried out using a derivatised amino acid unit directly or an amino acid unit which is firstly protected at the site intended for the derivatisation. When the synthesis of the peptide is complete, the final derivatisation with the active compound can then be carried out either in the solid phase or in solution after cleaving-off from the solid phase.

The bonding of the active compound in this case preferably takes place to the finished peptide, i.e. either still on the solid phase when the solid-phase synthesis of the peptide is complete or after the latter has been cleaved off in solution.

If the active compound is to be bonded, for example, to the N-terminal end of the peptide, the peptides are typically generated with an amino-terminal protecting group, such as, for example, Fmoc. If the active compound is able to withstand the conditions used on the one hand for cleaving off the peptide from the synthesis resin and on the other hand for deprotecting the side chains, the Fmoc group can be cleaved off from the N terminal of the complete resin-bonded peptide, enabling the active compound to be bonded to the free N-terminal amine. In such cases, the active compound is typically activated by processes which are generally known in the art for producing an active ester or active carbonate group which is effective for forming an amide or carbamate bond to the oligomer amino group. It is of course also possible to use a different linking chemistry.

In order to minimise side reactions here, guanidino and amidino groups may be blocked using conventional protecting groups, such as, for example, carbobenzyloxy groups (CBZ), di-t-BOC, PMC, Pbf, N—$NO_2$ and the like.

Coupling reactions are carried out by known coupling processes in solvents, such as, for example, N,N-dimethylformamide (DMF), N-methylpyrrolidone, dichloromethane and/or water. Illustrative coupling reagents include O-benzotriazolyloxytetramethyluronium hexafluorophosphate (HATU), dicyclohexylcarbodiimide, bromo-tris(pyrrolidino)phosphonium bromide (PyBroP), etc. Other reagents may be present, such as, for example, N,N-dimethylaminopyridine (DMAP), 4-pyrrolidinopyridine, N-hydroxysuccinimide or N-hydroxybenzotriazole.

If the molecule contains complexing agents, the metal ions can be complexed by known methods.

The present invention is based on the surprising effect that the peptides and conjugates according to the invention are enriched virtually exclusively in the kidney, for example after injection into the bloodstream or after subcutaneous injection. Accordingly, the peptides and/or conjugates according to the invention are suitable for use in therapeutic methods for treatment of the kidney, in imaging methods for depiction of the kidney and for renal targeting.

The present invention therefore also relates to a peptide or conjugate according to the invention, as described above, as medicament, such as, in particular, a therapeutic composition or an image-enhancing composition.

The present invention also relates to the use of a peptide or conjugate according to the invention, as described above, for targeting of the kidney. The targeting of the kidney here preferably serves for enriching medicaments for pharmaceutical or diagnostic applications in the kidney, i.e. for generating increased uptake in the kidney in relation to the remainder of the body.

Alternatively, the peptide alone without a bound active compound can also be enriched in the kidney. Owing to its high selectivity for the kidney, administration of the peptide therefore enables, for example, the enrichment of kidney-damaging substances which are administered during therapy to be prevented or at least reduced.

The present invention therefore also relates to the use of a peptide, as described above, for protection of the kidney.

In the radiopeptide therapy of neuroendocrine tumours, the substance DOTATOC, for example, is used. This octapeptide conjugated with DOTA has the undesired side effect of being taken up to the extent of about 20% by the kidneys (i.e. proximal tubule cells, PTCs). Damage in the kidneys is dose/therapy cycle-limiting here. The uptake of DOTATOC can be reduced if the peptide according to the invention is administered at the same time. Without being tied to the theory, it is thought that the receptor responsible for the uptake of the DOTATOC (megalin/cubilin) is blocked on the apical side of the PTCs and more DOTATOC therefore enters the urine.

The use of the conjugates according to the invention for targeting the kidney is advantageous compared with other known low-molecular-weight structures since they also exhibit very good concentration in the kidney in conjugation with the active compound. The comparison with peptides described in the literature which are taken up selectively by the kidneys (APASLYN (SEQ ID NO: 1) and HITSLLS (SEQ ID NO: 2), amino acids are indicated in single-letter code (Denby et al.: *Molecular Therapy* 15, 9, 2007, 1647-1654)) shows that, although most peptides have more or less highly pronounced kidney selectivity after intravenous administration, this is not the case in conjugation with an active compound. However, the pharmacological usefulness of the peptide structures as transport system for the treatment of kidney diseases only arises if these peptides are taken up together with conjugated active compounds virtually exclusively by the kidneys, namely the proximal tubule cells. Only in this case does a significant advantage arise over systemic administration of the active compound.

Furthermore, the conjugates according to the invention enable subcutaneous and intraperitoneal administration of the peptide/active compound conjugates according to the invention to successfully address the kidneys besides the intravenous administration of peptides/proteins described in the literature for active compound transport into the kidneys.

The intraperitonal, and specifically the subcutaneous administration route is advantageous for the administration of a potential active compound, compared with the intravenous route, for doctor and patient.

The present invention also relates to a medicament or a pharmaceutical composition, in particular a therapeutic or image-enhancing composition, comprising at least one peptide or conjugate according to the invention, as described above.

In accordance with the invention, the peptide or conjugate may also be in the form of its pharmaceutically usable salts and stereoisomers, including mixtures thereof in all ratios.

The use of the peptides and/or conjugates according to the invention for the preparation of a pharmaceutical composition or a medicament, in particular a therapeutic composition, and/or an image-enhancing composition (for example a contrast medium) and/or a radiolabelled tracer for nuclear-medical imaging is also in accordance with the invention.

In accordance with the invention, the present invention can also relate to a kit for the preparation of a medicament or a pharmaceutical composition, in particular a therapeutic or image-enhancing composition, comprising at least one peptide and/or conjugate according to the invention. This peptide and/or conjugate can then be reacted, for example, with a suitable active compound, depending on the application, for the preparation of a therapeutic or image-enhancing composition.

In accordance with the invention, image-enhancing composition or contrast medium or substances having an image-enhancing action are taken to mean substances or compositions which improve the depiction of the target organ in certain diagnostic methods, in general by increasing the contrast to the environment or increasing the signal of the target organ in relation to the environment.

The present invention additionally relates to the peptides and/or conjugates according to the invention, and/or pharmaceutically usable salts and stereoisomers thereof, including mixtures thereof in all ratios, and optionally excipients and/or adjuvants as medicament for use as medicament as active compound or active component in a medicament as diagnostic agent for use as diagnostic agent for use in the targeting of the kidney and in particular as medicament for the treatment of diseases of the kidney.

A therapeutic composition, a pharmaceutical composition or a medicament generally consists at least of the active compound—in this case the peptide or conjugate according to the invention with the bonded active compound—and one or more suitable solvents and/or excipients which allow application of the therapeutic composition.

A diagnostic composition or diagnostic agent serves as image-enhancing or imaging composition in diagnostic methods. A diagnostic agent generally consists at least of the signal source, i.e. the imaging and/or image-enhancing component—in this case the conjugate according to the invention, where in this case at least one active compound is preferably a complexing agent—and one or more suitable solvents and/or excipients which allow application of the diagnostic composition.

For diagnostic applications, the conjugate according to the invention preferably serves as signal source in an image-enhancing contrast medium, enabling the latter to be detected by means of nuclear-medical and/or radiological methods, such as SPECT, PET, ultrasound, and or also by magnetic resonance tomography, computer-tomographic and optical imaging methods (near-infrared imaging). Detection methods and applications of image-enhancing contrast media are known to the person skilled in the art. Examples of suitable applications are the diagnosis of cancer diseases, neurological questions, checking the response to a therapy, checking of the degree of damage of a kidney in the case of, for example, autoimmune diseases, and monitoring of gene therapies, but also the recognition of cellular changes.

Pharmaceutical compositions or medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or waterin-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or β-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity contains a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The peptides or conjugates according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The peptides or conjugates according to the invention can also be delivered using monoclonal antibodies as individual carriers to which the peptides or conjugates are coupled. The peptides or conjugates can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-ε-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

The peptides or conjugates according to the invention are preferably administered parenterally.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of the peptide or conjugate according to the invention depends on a number of factors, including the type of coupled active compound, the age and weight of the patient, the precise condition that requires treatment, and its severity, the nature of the formulation and the method of administration.

The present invention also relates to a kit for the preparation of a pharmaceutical composition, in particular an image-enhancing or therapeutic composition, at least comprising a peptide or conjugate according to the invention. If the conjugate contains a complexing agent, this has preferably not complexed any metal ions having an image-enhancing or therapeutic action. The peptide or conjugate according to the invention may be present in the kit in dissolved form in a solvent (for example an aqueous buffer) or preferably in the form of the lyophilisate.

Since the metal ions that are complexed by the complexing agent of the conjugate according to the invention are radioactive for many applications, pharmaceutical compositions which comprise the conjugate cannot be prepared as far in advance as desired. Furthermore, owing to the radioactivity, certain procedures regarding occupational safety must be followed during the preparation. For this reason, it is preferred in accordance with the invention to provide a kit which comprises the conjugate according to the invention, where the complexing agent has not yet complexed the metal ions necessary for the final application.

It has been found that the peptides or conjugates according to the invention have already concentrated specifically, i.e. exclusively or virtually exclusively, in the kidney a short time after application. In the case of the preferred intravenous administration of the conjugates according to the invention, concentration in the kidney is observed after only 5 minutes. After one hour, more than 30%, preferably more than 50%, particularly preferably more than 70%, very particularly preferably more than 80%, of the injected dose is located in the kidney (% data based on measurement of the radioactivity).

In organ distribution studies with radiolabelled conjugates according to the invention (for example PET measurements or other non-invasive imaging), the conjugates according to the invention typically exhibit at least a twofold, preferably at least a five-fold, particularly preferably at least a ten-fold concentration in the kidney in relation to the remainder of the body (blood, heart, lung, spleen, liver, muscle, brain) one hour after application. This means that the signal, which correlates directly with the amount of radiolabelled compound, in the kidney is at least twice as strong as the sum of the signals obtained from blood, heart, lung, spleen, liver, muscle and brain together.

The peptides or conjugates according to the invention can therefore be employed extremely well for diagnostic applications, such as renal scintigraphy, renal PET and renal MRT, functional testing of the kidney in general, for the therapy and diagnosis of renal cancer and, if desired, metastases of renal cancer, CT of the kidney and/or ultrasound of the kidney, and for specific targeting of the kidney.

The therapeutic application is, in particular, in the drug targeting for the organ the kidney. In particular, the peptides or conjugates according to the invention can serve as medicaments for the treatment of diseases of the kidney or of diseases in the treatment of which medicaments are employed whose site of action is the kidney. One or more active compounds, such as antibiotics, inflammation inhibitors, ACE inhibitors, diuretics, immunosuppressants or chemotherapeutic agents, are preferably bonded to the peptides according to the invention, for example via cleavable spacer sequences.

The use of the conjugates according to the invention for blocking the resorption of kidney-toxic substances is also possible.

The peptides according to the invention can furthermore also be employed to prevent or reduce the uptake of kidney-damaging substances into the kidneys.

In accordance with the invention, targeting of the kidney means the achievement of increased uptake of the applied substance in the kidney in relation to the remainder of the body. In the case of targeting of the kidney with the peptide or conjugate according to the invention, at least a 2-fold, preferably at least a 5-fold, particularly preferably at least a 10-fold concentration is preferably achieved in the kidney in relation to the remainder of the body (blood, heart, lung, spleen, liver, muscle, brain) by administration of a conjugate according to the invention. These values are determined by means of organ distribution studies with radiolabelled conjugates according to the invention (for example PET measurements or other non-invasive imaging). The concentration in the kidney typically takes place after 30 minutes to 8 hours, depending on the type of application.

FIGURES

Figure 3:
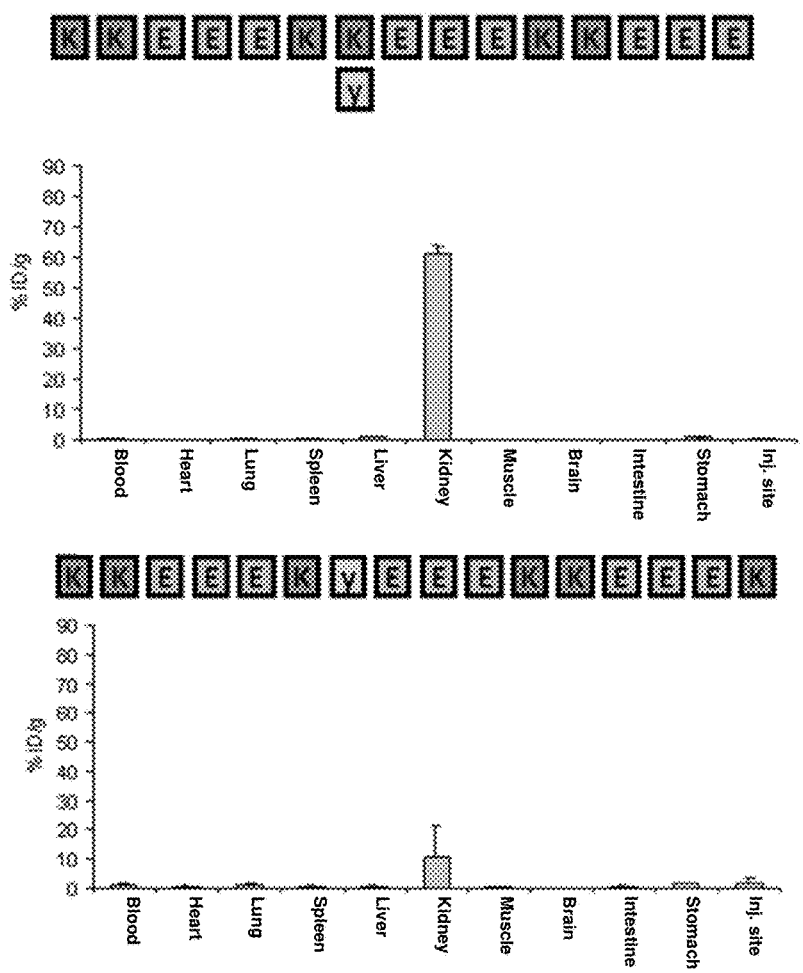

FIG. 3 compares the organ distribution of the two structures KKEEEKK(y)-EEEKKEEE (131-iodotyrosine branched in the chain) and KKEEEKyEEEKKEEEK (131-iodotyrosine linear in the chain) one hour after administration.

Figure 4:
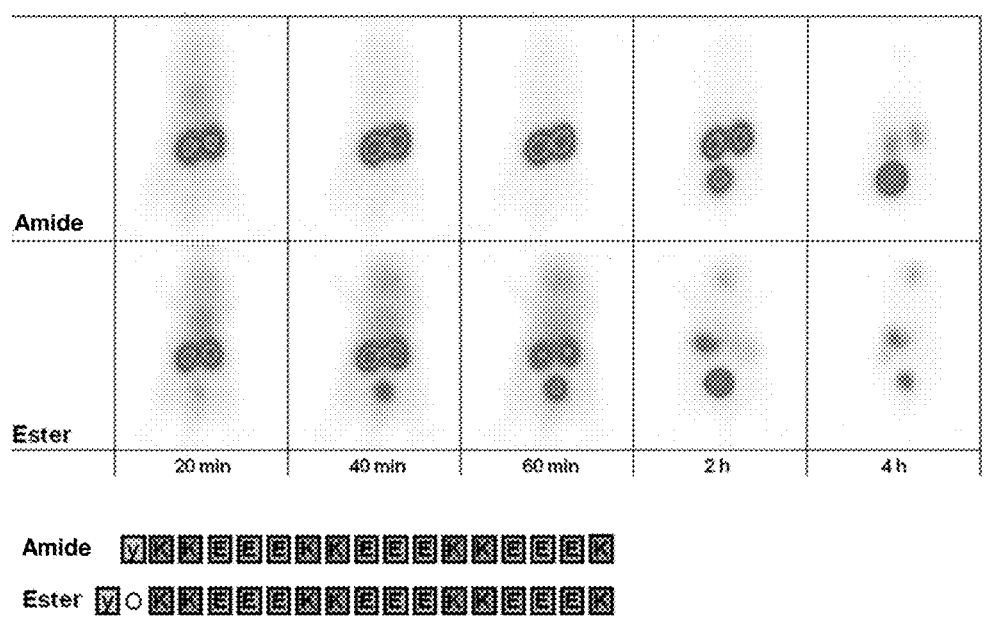

FIG. 4 compares the influence of the type of linking with reference to the structures y-KKEEEKKEEEKKEEEK (linking of the active compound via amide bonding, FIG. 4, top) and yoKKEEEKKEEEKKEEEK (linking of the active compound via ester bonding, FIG. 4, bottom).

Figure 5:
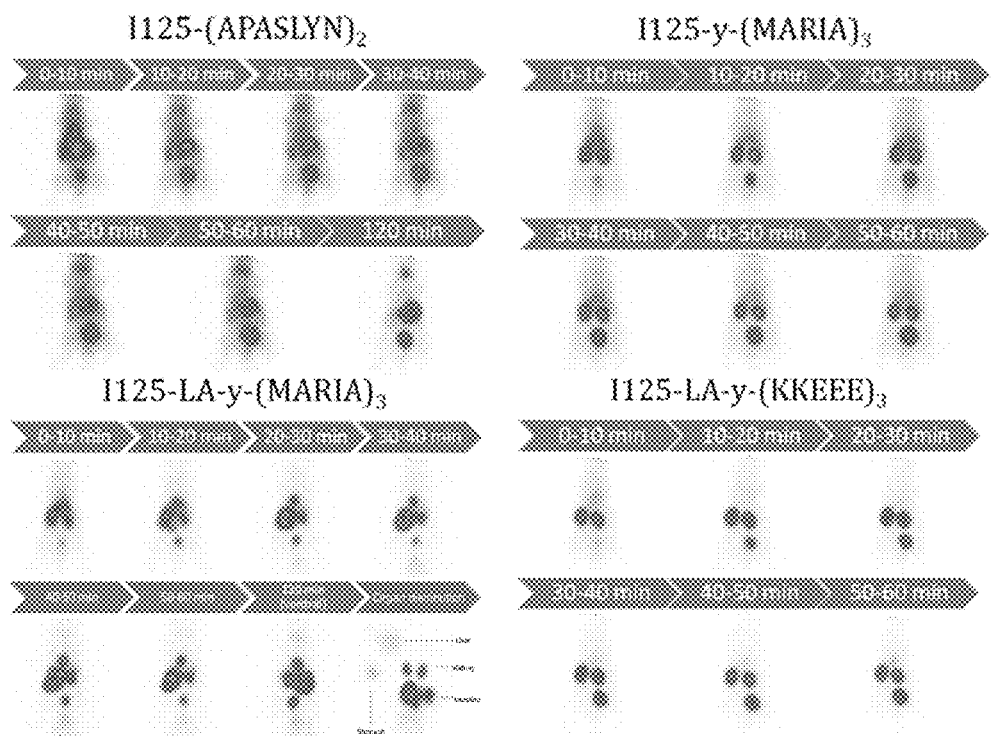

FIG. 5 compares the scintigraphic distribution of the peptides (APASLYN)$_2$ (SEQ ID NO: 90), y(MARIA)$_3$, y(MARIA)$_3$ as lipoic acid (LA) conjugate and y(KKEEE)$_3$ as lipoic acid conjugate in the animal model mouse after various times.

Figure 6:
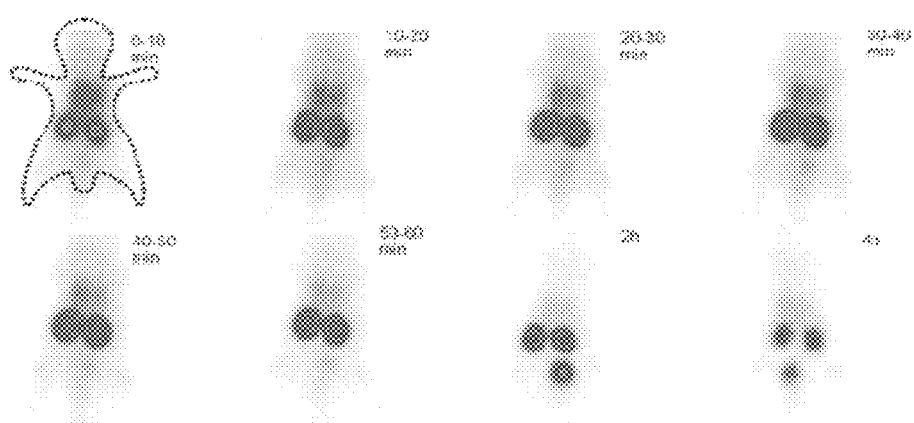

FIG. 6 shows the scintigraphic distribution of the peptide y(KKQQQ)$_3$K-NH$_2$ after administration.

Figure 7:
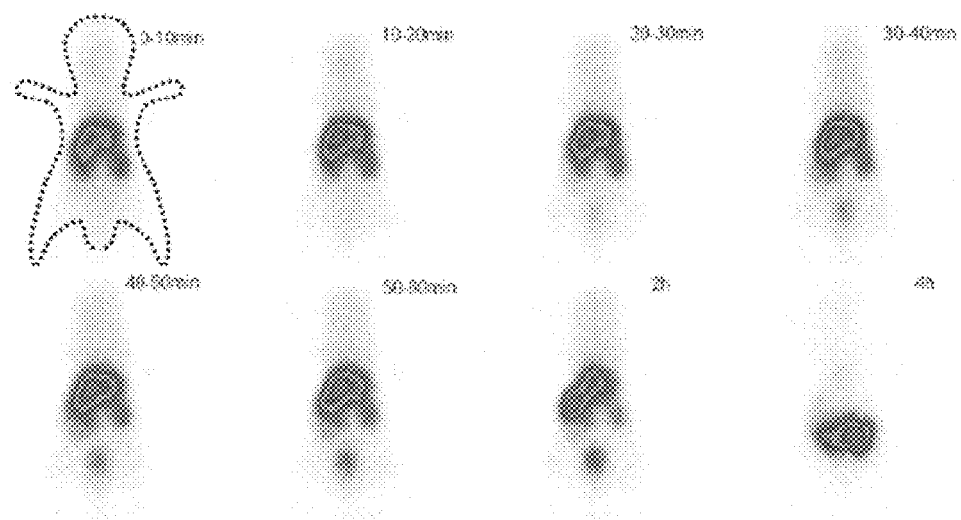

FIG. 7 shows the scintigraphic distribution of the peptide y(KKQQQ)$_3$K-NH$_2$ as lipoic acid conjugate after administration.

Figure 8:
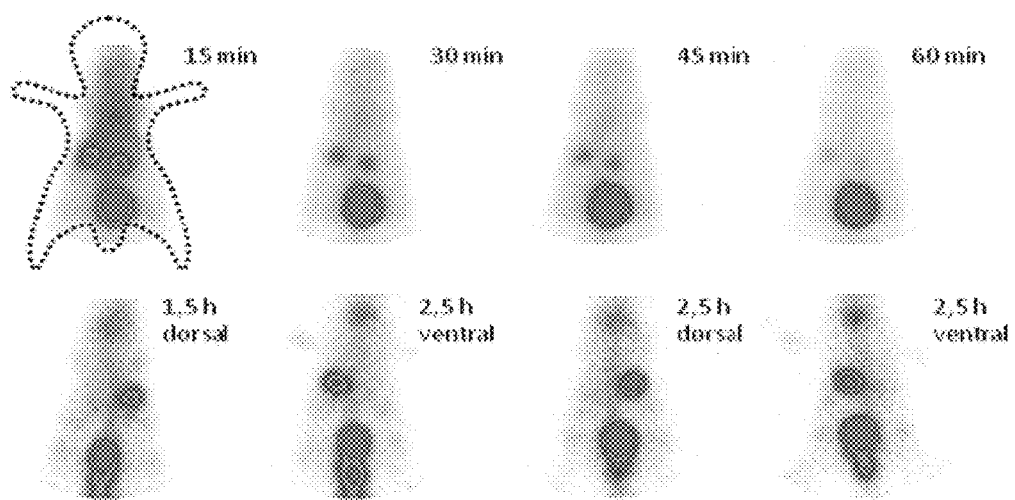

FIG. 8 shows the scintigraphic distribution of the peptide (yD$_8$) after intravenous administration to NMRI mice.

Figure 9:
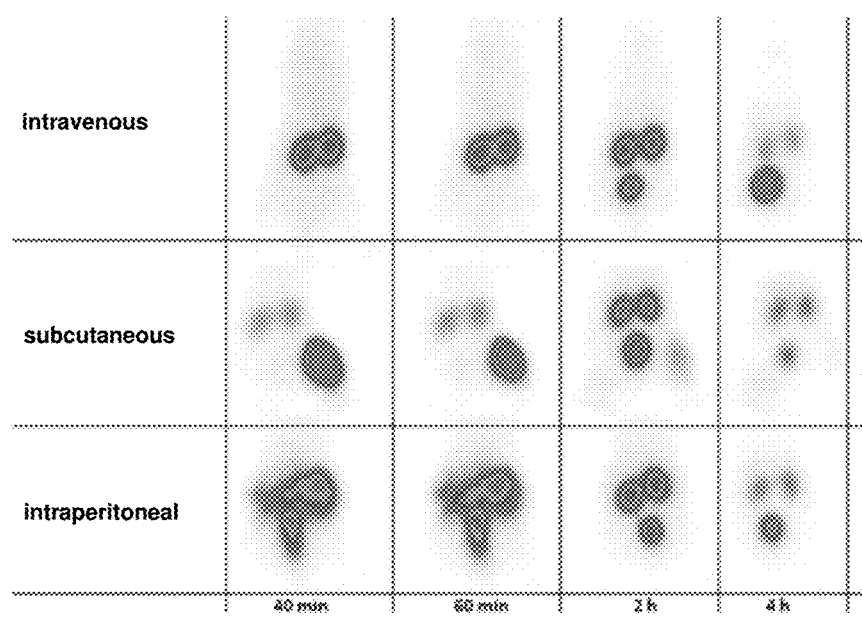

FIG. 9 compares the organ distribution of the 125-iodine-labelled conjugate y(KKEEE)$_3$K depending on the administration route.

Figure 10:
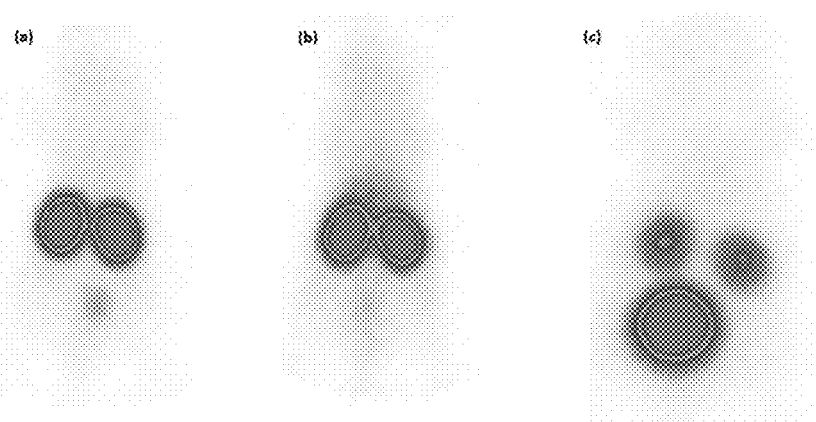

FIG. 10 compares the scintigraphic distribution of the peptides y(KKEE)$_5$K (FIG. 10a), y(KKKEE)$_3$K (FIG. 10b) and y(RREEE)$_3$R (FIG. 10c) radioactively labelled with iodine-125, in each case 1 hour after intravenous administration to NMRI mice.

Figure 11:
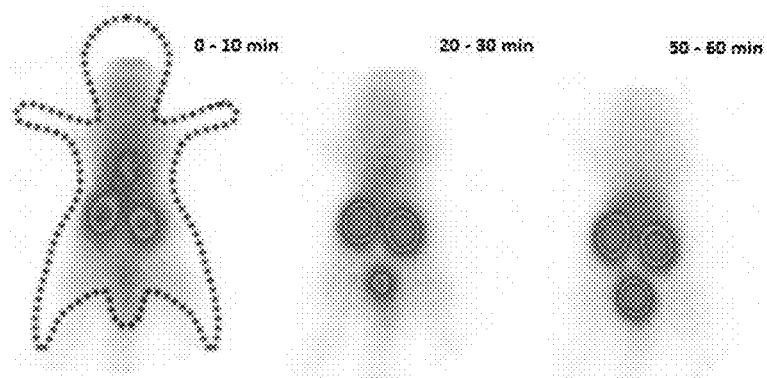

FIG. 11 shows the scintigraphic distribution of the diacetylcaffeic acid (KKEEE)$_3$K (SEQ ID NO: 85) active compound conjugate bonded at the N terminal after intravenous administration in an NMRI mouse.

Figure 12:
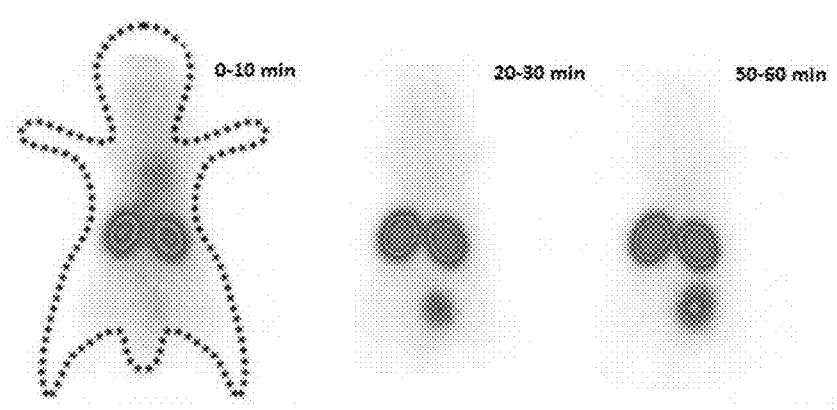

FIG. 12 shows the scintigraphic distribution of the diconjugated molecule yKKK(DCA)EEEKKEEEKKK(DCA)EEEK (CDA=diacetylcaffeic acid) after intravenous administration in an NMRI mouse.

Figure 13:
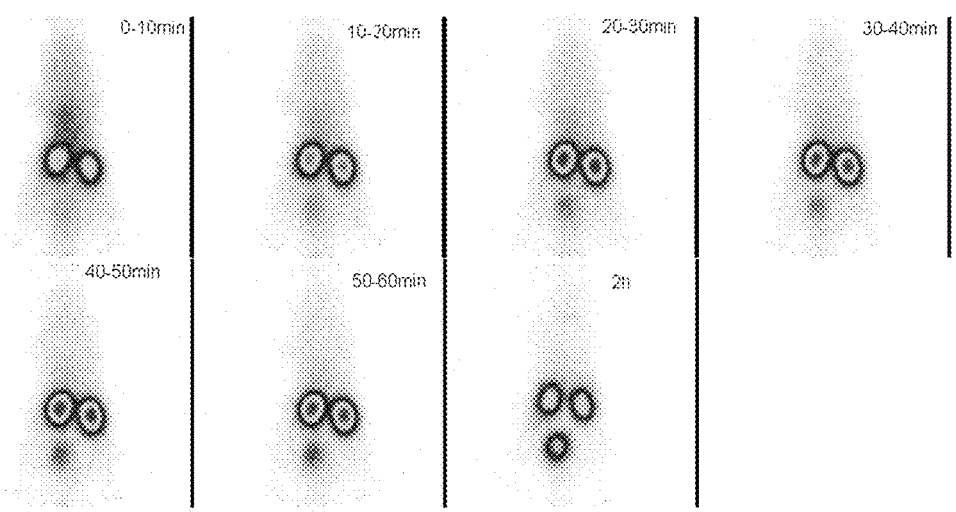

FIG. 13 shows the scintigraphic distribution of $^{125}$I-y(KKKε(lipoic acid)EEE)$_3$K after intravenous administration in an NMRI mouse.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

1. Material Syntheses 1.1. Solid-Phase Peptide Synthesis

The peptides are prepared on an ABI 433A fully automatic peptide synthesiser from Applied Biosystems GmbH (Carlsbad, Calif., USA) in accordance with the Fmoc/tBu strategy using Tentagel S RAM resin (degree of loading: 0.24 mmol/g; Rapp Polymere, Tübingen, Germany) as polymeric support. Fmoc-amino acids (Fmoc-AA-OH; Novabiochem, Merck KGaA, Darmstadt, Germany) containing acid-labile side-chain protecting groups (for example Arg(Pbf), Asn(Trt), Asp(OtBu), Cys(Trt), Gln(Trt), Glu(OtBu), His (Trt), Lys(Boc), Ser(tBu), Thr(tBu), Tyr(tBu)) are used as starting materials. The synthesis cycle consists of a) cleaving-off of the Fmoc protecting group using 20% piperidine in N-methyl-2-pyrrolidone (NMP), b) washing steps with NMP, c) coupling: Fmoc-AA-OH/2-(1H-benzotriazol-1-yl)-1,1,3,3-tetramethyluronium hexafluorophosphate (HBTU)/diisopropylethylamine (DIPEA)/peptide resin 10/10/20/1, 8 min, d) washing steps with NMP. The effectiveness of the cleaving-off of Fmoc are monitored by means of automatic conductivity measurements. The peptides are cleaved off from the resin using trifluoroacetic acid (TFA)/H$_2$O/triisopropylsilane (TIPS) (95/2.5/2.5) (2 h at room temperature), precipitated out in cold methyl tertbutyl ether (MTBE), separated by means of centrifugation (4000 rpm, 5 min), dried in vacuo and lyophilised from acetonitrile/H$_2$O (1:1). MAG3 is a peptide fragment comprising 3 glycine units and a thioglycolic acid derivative, which is prepared on the peptide synthesiser, as described above (i.e. the desired peptide sequence is extended by an MAG3 unit).

1.2 Purification and Characterisation of Peptides

The purification of the peptide cleaved off from the resin is carried out by means of semipreparative HPLC using an LaPrep unit (VWR GmbH, Darmstadt, Germany). The column used is a Waters XBridge BEH130 PREP C18 (5 µm, 19×150 mm) column (flow rates: 8-20 ml/min; solvent: 0.1% of TFA in water to 0.1% of TFA in acetonitrile). The separation is carried out using a gradient from water to acetonitrile which is matched to the physicochemical properties of the corresponding peptides. The purified peptide is obtained after lyophilisation.

For characterisation, the peptides prepared are analysed by means of analytical HPLC (Agilent 1100) and HPLC-MS (Exactive, Thermo Fisher Scientific). The HPLC analysis under standard conditions is carried out on the basis of a linear gradient from 0.1% of TFA in water to 0.1% of TFA in acetonitrile in 5 min (conditions: ChromolithR Performance RP-18e column, 100×3 mm; flow rate: 2 ml/min, wavelength=214 nm). For the mass spectrometry, an Agilent 1200 serves as HPLC system (conditions: Hypersil Gold C18 column, 0.21×200 mm, gradient: from 0.05% of TFA in water to 0.05% of TFA in acetonitrile in 30 min, flow rate: 200 µl/min, column oven: 60° C., wavelength=214 nm).

1.3 Radioactive Iodination of Peptides

The labelling is carried out using a 1 mM stock solution of the peptide to be labelled in water (dimethyl sulfoxide (DMSO) may have to be added for better solubility). Tyrosine-containing peptides are labelled with iodine-123, iodine-125 or iodine-131 (Perkin-Elmer, Waltham, Mass., USA) by means of the chloramine-T method. To this end, 20 µl of phosphate buffer (0.25 M, pH 7.4) are added to 10 µl of the stock solution, and the desired amount of radioactive iodine is added. For the labelling, 5 µl of chloramine-T (2 mg/ml of H$_2$O) are added. The reaction is carried out for 30 seconds and is subsequently terminated using 10 µl of a saturated methionine solution. In order to separate off free iodine and by-products, the reaction mixture is purified by means of semipreparative HPLC (Chromolith RP-18e, 100×4.6 mm). The separation is carried out using a linear gradient from 0.1% of TFA in water to 0.1% of TFA in acetonitrile in 10 minutes (flow rate: 2 ml/min, UV absorption at 214 nm, γ detection). The solvent is subsequently removed in a rotary evaporator, and the labelled peptide is taken up in the desired buffer.

1.4 Radioactive Labelling of MAG3 with $^{99m}$Technetium

For the labelling, 10 µl of a 1 mM peptide solution are added to 10 µl of phosphate buffer (0.5 M, pH 9). 4 µl of sodium tartrate (100 mg/ml of H$_2$O), 2 µl of lactose solution (100 mg/ml of H$_2$O) and 1 µl of SnCl$_2$ solution (10 mg/ml of SnCl$_2$×2 H$_2$O) are subsequently added. For the preparation of the SnCl$_2$ solution, 80 mg/ml are dissolved in concentrated hydrochloric acid with brief heating and diluted to 10 mg/ml with water. The required activity of $^{99m}$Tc (from technetium generator) is added, and the solution is subsequently heated at 95° C. for 30 min, purified by means of semi-preparative HPLC (see 1.3), freed from solvent and taken up in 300 µl of a sterile 0.9% NaCl solution.

1.5 Preparation of Lipoic Acid-y(KKEEE)$_3$K

The peptide y(KKEEE)$_3$K is prepared in a peptide synthesiser as described under 1.1 by means of solid-phase synthesis of the Fmoc/tBu strategy using the amino acids Fmoc-Lys(Boc)-OH, Fmoc-Glu(OtBu)-OH and Fmoc-Tyr(tBu)-OH (Novabiochem, Merck KGaA, Darmstadt, Germany). The peptide is initially not cleaved off from the resin, but instead suspended in NMP after the final Fmoc deprotection (1 ml of NMP are used per 100 mg of peptide resin). (RS)-lipoic acid (Merck KGaA, Darmstadt, Germany; in the meantime 4 equivalents based on the resin loading) is dissolved in NMP (1 ml per 100 mg), HBTU (4 eq.) is added, and the mixture is stirred at room temperature for about 10 min. The reaction mixture is added to the peptide resin, DIPEA (10 eq.) is added, and the mixture is shaken at room temperature for about 4 h. The resin is washed 5× with NMP and 5× with dichloromethane (DCM) and dried in vacuo for about 4 h. The lipoic acid/peptide conjugate is cleaved off from the resin using TFA/thioanisole/anisole (90/8/2) at room temperature for about 1 h, precipitated out in cold MTBE, separated by means of centrifugation (4000 rpm, 5 min), dried in vacuo, lyophilised from acetonitrile/H$_2$O (1:1) and purified as described under 1.2. Conjugates with other active compounds can also be prepared analogously.

1.6 Preparation of yKKK(Diacetylcaffeic Acid)(EEEKK)$_2$K(Diacetylcaffeic Acid)EEEK For the peptic conjugation of diacetylcaffeic acid onto a lysine side chain, the amino acid Fmoc-Lys(Mmt)-OH is incorporated into the sequence of the peptide backbone. Before the cleaving-off, dichloromethane (DCM)/triisopropylsilane/TFA (94:5:1) is added to the peptide resin prepared under 1.1 for 3 min, and the mixture is washed 5× with DCM. This operation is repeated 3×. For coupling to the orthogonally deprotected side chain of lysine, 4 eq of diacetylcaffeic acid are dissolved in NMP, 4 eq of 1-ethyl-3-(3-dimethylaminopropyl)carbodiimide (EDC), 4 eq of ethyl cyano(hydroxyimino)acetate (Oxyma Pure) and 10 eq of diisopropylethylamine (DIPEA) are added, the mixture is stirred at room temperature for about 10 min and subsequently added to the peptide resin. The reaction mixture is shaken at room temperature for about 1 h, washed 5× with NMP and 5× with DCM and dried in vacuo. The functionalised peptide is cleaved off from the resin as described under 1.1 and purified as described under 1.2.

Conjugates with other active compounds can also be prepared analogously.

1.7 Preparation of y(KKKε(Lipoic Acid)EEE)$_3$K

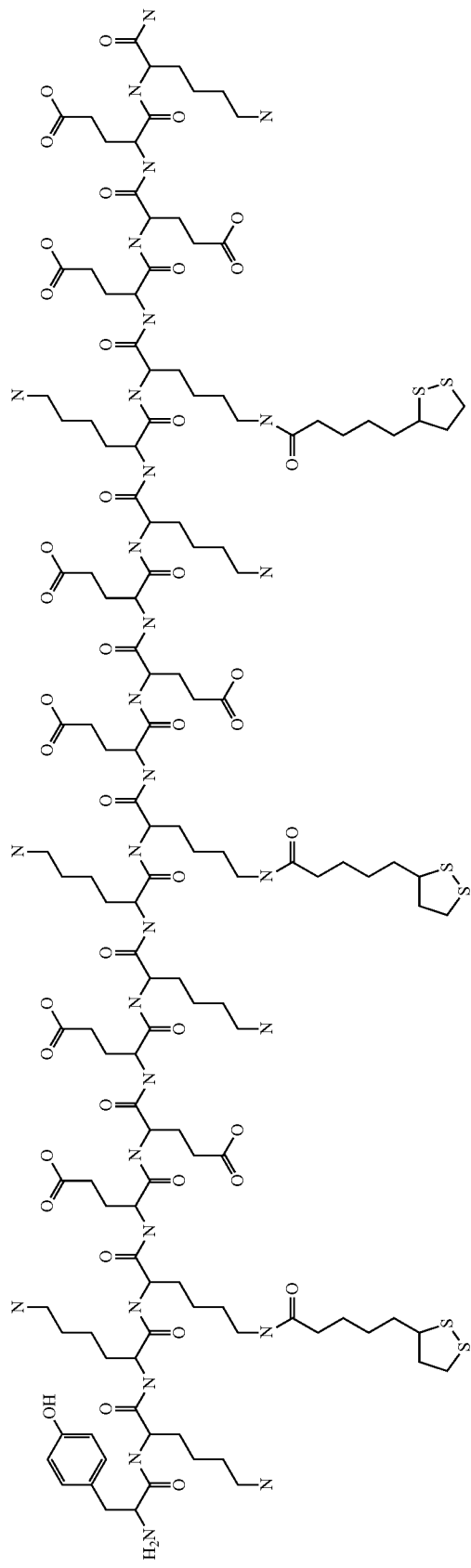

1.7.1 Synthesis of the Fmoc-Lysine(ε-Lipoic Acid)-OH Building Block

N-Hydroxysuccinimide (1.15 g, 10 mmol), α-lipoic acid (2.02 g, 9.8 mmol) and (1.92 g, 10 mmol) of 1-ethyl-3-(3-dimethylaminopropyl)carbodiimide (EDAC) are dissolved in 50 ml of DMF and stirred at room temperature for about 4 h. 60 ml of ethyl acetate are then added to the batch. The organic phase is washed three times with 60 ml of distilled water, three times with 60 ml of saturated sodium hydrogencarbonate solution and once with saturated sodium chloride solution. The ethyl acetate phase is dried over $Na_2SO_4$, filtered and evaporated to dryness.

Yield: 2.23 g (73.5%)

Fmoc-Lys-OH (2.65 g, 7.2 mmol) is suspended in 110 ml of HEPES buffer (pH=7.4), and (2.14 g, 7.05 mmol) of lipoic acid active ester (dissolved in 130 ml of acteone) are added, and the mixture is stirred at room temperature. After a reaction time of about 3 h, the solution is adjusted to pH 7 by means of 0.1 N NaOH solution and stirred at room temperature for about 20 h. The batch is then brought to pH 9 using 0.1 N NaOH and washed twice with about 30 ml of ethyl acetate, subsequently adjusted to pH 3 using 1 N HCl and extracted three times with about 40 ml of ethyl acetate. The combined org. phases are washed with saturated sodium chloride solution, dried over Na2SO4, filtered and evaporated to dryness.

Weight of crude product: 4.14 g (103. 25%)

The purification of the crude product is carried out by flash chromatography (stationary phase: silica gel 60, particle size: 15-40 µm, pre-packed by Götec-Labortechnik GmbH, mobile phase: chloroform, methanol (comprising 0.1% of HOAc), flow rate: 60 ml/min, loading: about 2 g, gradient: from 100% to 75% of chloroform in 18 min). The product fractions (Rt=9.1 min) are combined and evaporated to dryness.

Product weight: 3.18 g (77%)

1.7.2 Solid-Phase Peptide Synthesis

Peptides are prepared using a synthesiser from Applied Biosystems GmbH (Carlsbad, Calif., USA), model 433A, using the Fmoc/tBu strategy. The reactive side chains of the amino acids are protected as follows: Lys(Boc), Glu(tBu) and Tyr(tBu). Rink amide resin from Rapp-Polymere GmbH (degree of loading: 0.24 mmol/g) serves as solid phase. The corresponding amino acids, the Fmoc-lysine(ε-lipoic acid)-OH building block and HBTU are employed in 4-fold excess. The solvent used is NMP, and piperidine (20% in NMP) is used for the respective Fmoc cleaving off.

The protected peptide is cleaved off from the resin using TFA:thioanisole:anisole=90:8:2 (1 ml per 100 mg) (1-2 h), precipitated out in MTBE, centrifuged and dried.

1.7.3 Radioactive Iodination of Peptides

The tyrosine-containing peptides are labelled with $^{125}$iodine by means of the chloramine-T method. For the labelling, a 1 mM stock solution in water is used. If necessary, DMSO is added for better solubility. To this end, 20 µl of phosphate buffer (0.25 M, pH 7.4) are added to 10 µl of the stock solution, and the desired amount of radioactive iodine is added. The labelling is carried out using 5 µl of chloramine-T (2 mg/ml of $H_2O$). The reaction is carried out for 30 seconds and is subsequently terminated using 10 µl of a saturated methionine solution.

After the labelling, the peptide is purified by means of semi-preparative HPLC in order to remove the excess free iodine and other by-products. 100 µl of the 0.1 mM stock solution are in each case used for the injection. Before the injection, the radioactivity is recorded by means of a Geiger counter.

Conjugates with other active compounds can also be prepared analogously.

2. Use Examples

2.1. Organ Distribution Studies

In order to determine the pharmacokinetics, the radioactively labelled molecules to be investigated are injected into female NMRI mice via the tail vein (about 100 µl per animal). The animals (n=3 per time point) are subsequently sacrificed at the corresponding time points, dissected, and the distribution of the radioactivity in the isolated organs (liver, kidney, lung, spleen, intestine, brain, heart, blood, . . . ) is quantified by γ counter (Berthold LB951 G). The radioactivity measured per gram of organ/tissue based on the injected dose (ID) is determined and quoted as % of ID/g.

2.2 Influence of the Chain Length and Linking Site of the Active Compound

In further experiments, the molecular structure is modified.

The structures MAG3-KKEEEKKEEEKKEEEK (SEQ ID NO: 85), MAG3-KKEEEKKEEEKKEEEKKEEEK-KEEEKKEEE (SEQ ID NO: 89) and y-KKEEEKKEEEK-KEEEK (N-terminal linking of the active compound FIG. 1, top and FIG. 2 bottom) and the structures KKEEEK-KEEEKKEEE-y and KKEEEKKEEEKKEEEKKEEEK-KEEEKKEEE-y (C-terminal linking of the active compound FIG. 1, bottom and FIG. 2, top) are investigated y here stands for D-tyrosine; MAG3 stands for a peptide fragment which complexes $^{99m}$Tc.

Figure 1:
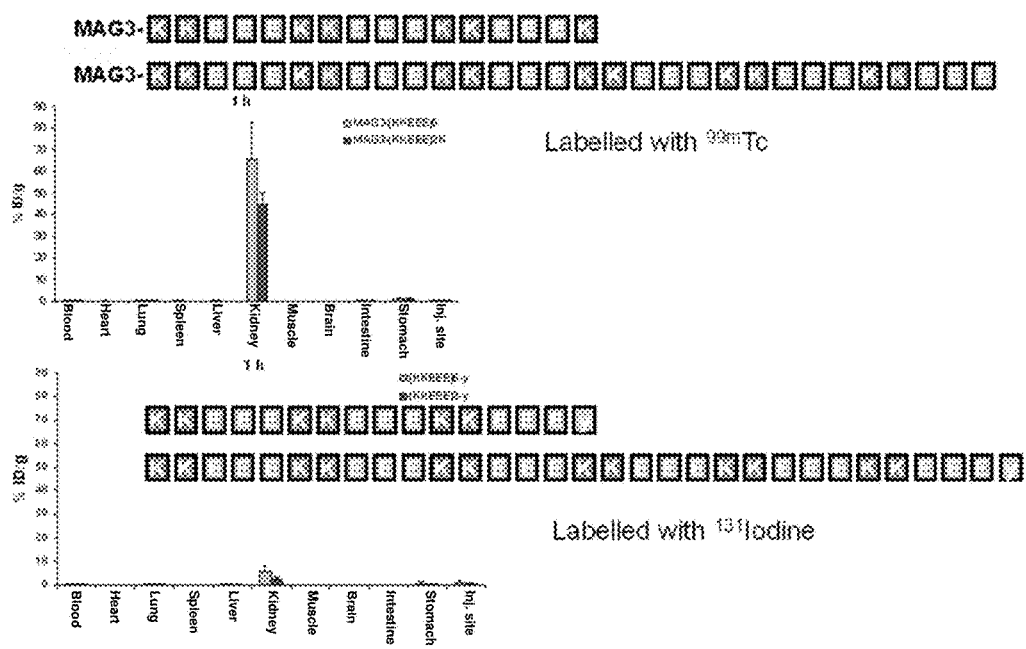
FIG. 1 shows the influence of the chain length on the release of active compound for the structures MAG3-KKEEEKKEEEKKEEEK (SEQ ID NO: 85) and MAG3-KKEEEKKEEEKKEEEKKEEEKKEEEKKEEE (SEQ ID NO: 89) (N-terminal linking of the active compound FIG. 1, top) and KKEEEKKEEEKKEEE-y and KKEEEKKEEEK-KEEEKKEEEKKEEEKKEEE-y (C-terminal linking of the active compound—FIG. 1, bottom).
Figure 2:
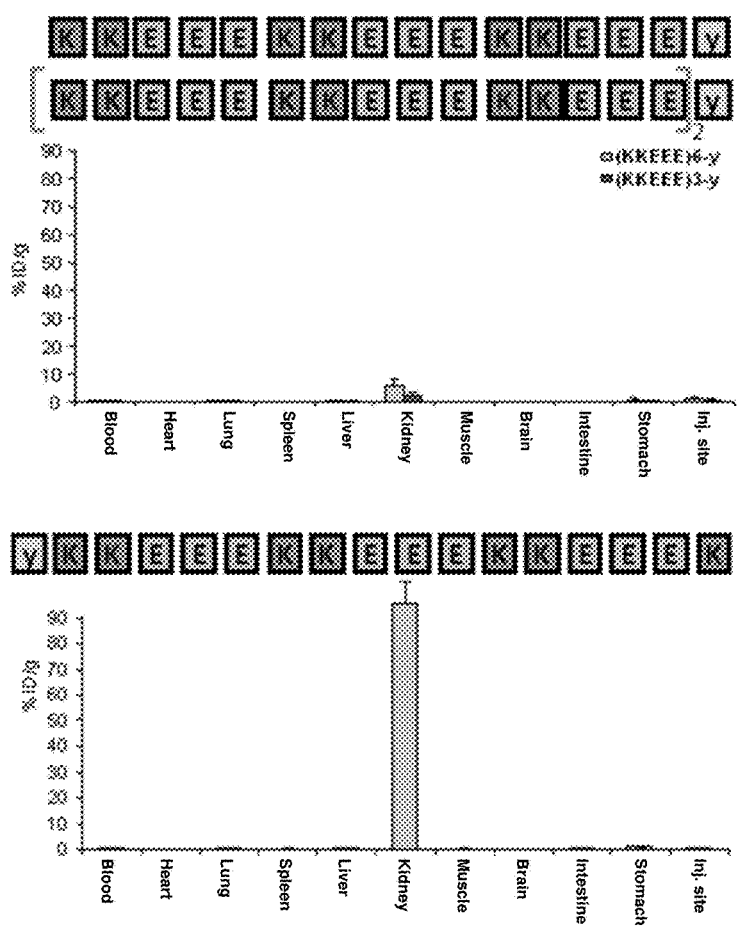
FIG. 2 shows the influence of the chain length on the release of active compound for the structure y-KKEEEK-KEEEKKEEEK (N-terminal linking of the active compound—FIG. 2, bottom) and the structures KKEEEK-KEEEKKEEE-y and KKEEEKKEEEKKEEEKKEEEKKEEEKKEEE-y (C-terminal linking of the active compound—FIG. 2, top).

The result is depicted in FIGS. 1 and 2 (ID/g here stands for "injected dose per gram of tissue): the release of radiolabelled tyrosine (as "active compound") is strongly influenced on the one hand via the chain length and on the other hand via the linking site of the "active compound" (C or N terminal). Basically, longer peptides result in delayed release. In addition, the release of tracers linked at the C terminal (iodotyrosine or also MAG3 with $^{99m}$Tc) proceeds significantly more quickly than in the case of N-terminal linking. The rate-determining step in the peptide degradation is apparently influenced, in particular, by carboxypeptidases, which break down the peptide starting from the C terminal.

The release kinetics of an active compound can be intentionally adjusted through the molecular structure of the peptide and the linking site of the active compound (C or N terminal).

2.3. Influence of the Degree of Branching

The enzymatic degradation of branched peptide structures is fundamentally significantly more difficult than the degradation of linear peptides. For this purpose, a comparative experiment is carried out in which the model active compound radioiodotyrosine was incorporated into the chain in a linear manner or into the chain in a branched manner. The structures KKEEEKK(y)-EEEKKEEE and KKEEEKy-EEEKKEEEK are investigated.

The result is shown in FIG. 3: the figure shows the organ distribution one hour after administration. The radioiodotyrosine incorporated into the chain in a branched manner (FIG. 3, top) is broken down significantly more slowly here than the linear radioiodotyrosine (FIG. 3, bottom).

2.4. Influence of the Type of Linking

The structures y-KKEEEKKEEEKKEEEK (linking of the active compound via amide bonding) and yoKKEEEKKEEEKKEEEK (linking of the active compound via ester bonding) are investigated.

The result is shown in FIG. 4: for the binding of active compounds which are to be released rapidly, the incorporation of a readily cleavable ester link of the active compound to the active compound transporter has proven advantageous (FIG. 4, bottom). The breaking of the ester link takes place more quickly in terms of time than the breakdown of the active compound transporter by proteases.

2.5. Comparative Experiments

In order to be able to compare the kidney specificity of the peptides mentioned in the literature with the structures according to the invention, the peptides APASLYN (SEQ ID NO: 1) and HITSLLS (SEQ ID NO: 2) known in the literature (Denby et al.: Molecular Therapy 15, 9, 2007, 1647-1654) are prepared with the aid of an Applied Bioscience peptide synthesiser, model 433A, and conjugated with a real active compound. The peptide sequences are built up by means of Fmoc strategy, and the active compound is conjugated to the carrier by solid-phase reaction. As further comparison, any desired peptide sequence y(MARIA)$_3$ having 16 amino acids is selected. In the cases where no tyrosine is present for radiolabelling in the peptide (HITSLLS (SEQ ID NO: 2)), a D-tyrosine is additionally inserted. The active compound used is (RS)-lipoic acid, (abbr.: LA).

FIG. 5 shows the SPECT recordings of the distribution of the peptides (APASLYN)$_2$ (SEQ ID NO: 90) and y(MARIA)$_3$ in the animal model mouse after various times. In the example of (APASLYN)$_2$ (SEQ ID NO: 90), the kidney selectivity of the peptide is already inadequate without active compound lipoic acid. Although the freely selected peptide sequence y(MARIA)$_3$ has good kidney selectivity, this is, however, substantially lost after conjugation with lipoic acid. By comparison, the kidney selectivity in the structure (KKEEE)$_3$ (SEQ ID NO: 91) according to the invention is retained even with conjugated lipoic acid.

In a further experiment, the glutamic acid in the peptide y(KKEEE)$_3$K-NH$_2$ is replaced by glutamine. The resultant peptide y(KKQQQ)$_3$K-NH$_2$ contains no acid groups. The uptake of the peptide per se and of the peptide conjugated with lipoic acid is investigated.

Result (see FIGS. 6 and 7): after labelling of the peptide with radioiodine, high uptake of the peptide into the kidneys can be detected by means of imaging (FIG. 6). After conjugation of the peptide with the active compound lipoic acid, however, this kidney specificity is lost virtually completely (FIG. 7).

In a further experiment, a peptide which is built up only from amino acids carrying acid groups (yD$_8$) is synthesised. This peptide is likewise labelled with radioiodine and administered intravenously to NMRI mice.

FIG. 8 shows the result: after only 15 minutes, the majority of the administered radioactivity is located in the bladder of the experimental animals. A peptide built up entirely from acidic amino acids is apparently excreted very rapidly via the kidneys and not resorbed by the proximal tubule cells of the kidneys. A purely acidic molecular structure of this type is apparently not suitable for the transport of active compounds into the proximal tubule cells.

2.6. Scintigraphic Distributions of y(KKEE)$_5$K, y(KKKEE)$_3$K and y(RREEE)$_3$R In further experiments, the acid/base ratio is varied and lysine is replaced by arginine. The following peptides are investigated here: y(KKEE)$_5$K, y(KKKEE)$_3$K and y(RREEE)$_3$R.

Result (see FIG. 10, 1 h values after respective radioactive labelling of the peptides with iodine-125 and scintigraphic investigation after intravenous administration to female NMRI mice): the change in the acid/base ratio from 1:1 (y(KKEE)$_5$K) (FIG. 10 (a)) to 2:3 (y(KKKEE)$_3$K) (FIG. 10 (b)) does not detectably change the kidney selectivity of the peptides. On replacement of the lysine by arginine (y(RREEE)$_3$R), however, the majority of the administered radioactivity is located in the bladder of the experimental animals after 1 h. The high kidney specificity is retained, no other organ is addressed, but the renal elimination appears to be accelerated by the replacement of the amino acid (see FIG. 10 (c)).

2.7. Scintigraphic Distribution of Diacetylcaffeic Acid Conjugates

In further experiments, the potential active compound diacetylcaffeic acid (DCA) is bound to lysine side chains of the peptide backbone both at the N terminal and also multiply. The preparation of the N-terminal conjugate with y(KKEEE)$_3$K is carried out analogously as described under 1.5.; the preparation of the diconjugated molecule (structure: yKKK(DCA)EEEKKEEEKKK-(DCA)EEEK) is carried out analogously as described under 1.6. The peptide/active compound conjugates obtained in this way are investigated for their kidney selectivity after labelling by means of iodine-125 and intravenous administration in the animal model mouse.

Result (see FIGS. 11 and 12): the peptide/active compound conjugates prepared retain their high kidney specificity both after N-terminal binding of diacetylcaffeic acid (FIG. 11) and also in the case of double binding of diacetylcaffeic acid to different side chains of lysine of the peptide backbone (FIG. 12).

2.8. Administration Route

In further experiments, the administration route is investigated. To this end, nine NMRI mice are divided into three groups. All animals receive 10 mg/kg of body weight of a conjugate of D-tyrosine bonded to (KKEEE)3K (SEQ ID NO: 85) at the N terminal. Part of the conjugate is labelled with a radioactive iodine isotope on the D-tyrosine by means of the chloramine-T method. The labelled conjugate is administered intravenously to group 1, subcutaneously to group 2 and intraperitoneally to group 3. The conjugate here is dissolved in 100 µl of PBS buffer. SPECT scans of animals from the respective group are then carried out at various times (40, 60, 120 and 240 minutes). The results of this experimental series are depicted in FIG. 9.

Besides the intravenous administration of peptides/proteins described in the literature for transport of active compound into the kidneys, subcutaneous and intraperitoneal administration of the peptides or peptide/active compound conjugates according to the invention can also successfully address the kidneys.

2.9 Scintigraphic Distribution of Lipoic Acid Conjugates in Accordance with Example 1.7

In further experiments, the potential active compound lipoic acid is bonded via the lysine side chains of the peptide backbone. The preparation of the conjugate y(KKKε(lipoic acid)EEE)$_3$K is carried out as described in Example 1.7. The peptide/active compound conjugate obtained in this way is investigated for its kidney selectivity after labelling by means of iodine-125 and intravenous administration in the animal model mouse.

Result (see FIG. 13): the peptide/active compound conjugate prepared has high kidney specificity.

The invention claimed is:

1. A peptide comprising 3 to 5 sequence sections selected from the group consisting of -(KKEEE)- (SEQ ID NO: 76), -(RREEE)- (SEQ ID NO: 77), -(KKEE)- (SEQ ID NO: 78), -(KKKEEE)- (SEQ ID NO: 79) and -(KKKEE)-(SEQ ID NO: 80), wherein more than 90% of amino acids in the peptide are the selected sequence sections,
wherein
E is glutamic acid,
K is lysine, and
R is arginine.

2. The peptide according to claim 1, which contains 3 to 5 successive sequence sections selected from the group consisting of -(KKEEE)- (SEQ ID NO: 76), -(RREEE)- (SEQ ID NO: 77), -(KKEE)- (SEQ ID NO: 78), -(KKKEEE)- (SEQ ID NO: 79) and -(KKKEE)- (SEQ ID NO: 80).

3. The peptide according to claim 1, which contains sequence sections selected from the group consisting of -(KKEEE)- (SEQ ID NO: 76), —(KKEE)- (SEQ ID NO: 78), -(KKKEEE)- (SEQ ID NO: 79) and -(KKKEE)- (SEQ ID NO: 80), wherein more than 90% of amino acids in the peptide are the selected sequence sections.

4. The peptide according to claim 1, which contains sequence sections -(RREEE)- (SEQ ID NO: 77), wherein more than 90% of amino acids in the peptide are said sequence sections.

5. The peptide according to claim 1, which is selected from the group consisting of (RREEE)$_3$R (SEQ ID NO: 81), (KKEE)$_5$K SEQ ID NO: 82), (KKKEE)$_3$K (SEQ ID NO: 83), (KKKEEE)$_3$K (SEQ ID NO: 84) and (KKEEE)$_3$K (SEQ ID NO: 85).

6. A conjugate containing at least one peptide and at least one active compound which is covalently bonded, optionally via a spacer, wherein the at least one peptide comprises 3 to 5 sequence sections selected from the group consisting of -(KKEEE)- (SEQ ID NO: 76), -(RREEE)- (SEQ ID NO: 77), -(KKEE)- (SEQ ID NO: 78), -(KKKEEE)- (SEQ ID NO: 79) and -(KKKEE)- (SEQ ID NO: 80), wherein more than 50% of amino acids in the peptide are the selected sequence sections,
wherein
E is glutamic acid,
K is lysine, and
R is arginine.

7. The conjugate according to claim 6, wherein the active compound is selected from the group consisting of immunosuppressants, cytostatics, immunotherapeutic agents, antiphlogistics, antibiotics, virostatics, anti-hypertensives, ACE inhibitors, sartans, renin inhibitors, protein kinase inhibitors, uricosurics, diuretics and antifibrotics.

8. A conjugate according to claim 6, wherein the at least one active compound is bonded to the N terminal and/or the C terminal of the peptide.

9. A conjugate according to claim 6, wherein the at least one active compound is bonded to an amino acid within the chain.

10. A conjugate according to claim 6, wherein the active compound is bonded via an ester link.

11. A process for preparing the conjugate according to claim 6, comprising conjugating an optionally activated active compound to the peptide.

12. A pharmaceutical composition comprising a peptide according to claim 1 and a pharmaceutically acceptable carrier.

13. A pharmaceutical composition comprising a conjugate according to claim 6 and a pharmaceutically acceptable carrier.

14. A method for targeting a kidney, comprising administering to a subject in need thereof an effective amount of a peptide according to claim 1 or a conjugate containing said peptide and at least one active compound which is covalently bonded, optionally via a spacer.

15. A method for protecting a kidney, comprising administering to a subject in need thereof an effective amount of a peptide according to claim 1.

16. A method for enhancing an image, comprising administering to a subject in need thereof an effective amount of an image-enhancing composition, comprising at least one peptide according to claim 1 or a conjugate containing said peptide and at least one active compound which is covalently bonded, optionally via a spacer.

17. A method for targeting a kidney, comprising administering to a subject in need thereof an effective amount of a conjugate according to claim 6.

18. A method for enhancing an image, comprising administering to a subject in need thereof an effective amount of an image-enhancing composition, comprising at least one conjugate according to claim 6.

19. The peptide according to claim 1, which contains 3 to 5 sequence sections selected from the group consisting of -(KKEEE)- (SEQ ID NO: 76), -(RREEE)- (SEQ ID NO: 77), -(KKKEEE)- (SEQ ID NO: 79) and -(KKKEE)- (SEQ ID NO: 80), wherein more than 90% of amino acids in the peptide are said sequence sections.

20. The conjugate according to claim 6, wherein the active compound is selected from the group consisting of azathioprine, mycophenolate-mofetil, ciclosporin, tacrolimus, sirolimus, fingolimod, triptolide, atrasentan, nintedanib, bleomycin, dactinomycin, mitomycin, daunorubicin, doxorubicin, epirubicin, idarubicin, mitoxantron, amsacrine, doxofluridine, cisplatin, carboplatin, oxaliplatin, satraplatin, camptothecin, toptecan, irinotecan, etoposide, teniposide, cyclophosphamide, trofosfamide, melphalan, chlorambucil, estramustine, busulfan, chlorambucil, chlormethine, treosulfan, carmustine, lomustine, nimustine, procarbazine, streptozocine, dacarbazine, ifosfamide, temozolomide, thiotepa, vinorelbine, vincristine, vinblastine, vindesine, paclitaxel, docetaxel, methotrexate, pemetrexed, raltitrexed, fluorouracil, capecitabine, cytosinarabinoside, gemcitabine, tioguanine, pentostatin, mercaptopurine, fludarabine, caldribine, hydroxycarbamide, mitotane, azacitidine, cytarabine, nelarabine, bortezomib, anagrelide, imatinib, erlotinib, sunitinib, sorafenib, dasatinib, lapatinib, nilotinib, cetuximab, alemtuzumab, bevacizumab, naproxen, ibuprofen, indometacin, prednisolone, prednisone, hydrocortisone, budesonide, benzylpenicillin, methicillin, amoxicillin, cefuroxim, cefotaxim, cefadroxil, cefixim, clavulanic acid, sulbactam, tazobactam, imipenem, meropenem, aztreonam, tetracycline, chlortetracycline, oxytetracycline, doxycycline, minocycline, tigecycline, erythromycin A, vancomycin, calicheamicin, aciclovir, valaciclovir, ganciclovir, valganciclovir, penciclovir, famciclovir, brivudine, cidofovir, foscarnet, idoxuridine, tromantadine, benazepril, captopril, cilazapril, enalapril, fosinopril, lisinopril, perindopril, quinapril, ramipril, trandolapril, zofenopril, losartan, balsartan, irbesartan, candesartan, eprosartan, olmesartan, telmisartan, aliskiren, proproanolol, pindolol, sotalol, bopindolol, atenolol, bisorpolol, celiprolol, esmolol, metoprolol, nebivolol, oxprenolol, carvedilol, labetalol, probenecid, benzbromarone, acetazolamide, furosemide, torasemide, bumetanide, piretanide, azosemide, etacrynic acid, etozoline, hydrochlorothiazide, benzthiazide, chlorothiazide, chlorthalidone, indapamide, mefruside, metolazone, clopamide, xipamide, hydroflumethiazide, methyclothiazide, polythiazide, amiloride, triameterene, spironolactone, canrenone, eplerenone, spironolactone, pirfenidone and seliciclib.

\* \* \* \* \*